United States Patent
Beadle et al.

(10) Patent No.: US 7,432,280 B2
(45) Date of Patent: Oct. 7, 2008

(54) 3-AMINOPIPERIDINES AND 3-AMINOQUINUCLIDINES AS INHIBITORS OF MONOAMINE UPTAKE

(75) Inventors: Christopher David Beadle, Basingstoke (GB); Manuel Javier Cases-Thomas, Basingstoke (GB); Barry Peter Clark, Basingstoke (GB); Peter Thaddeus Gallagher, Basingstoke (GB); John Joseph Masters, Fishers, IN (US); Graham Henry Timms, Basingstoke (GB); Magnus Wilhelm Walter, Basingstoke (GB); Maria Ann Whatton, Basingstoke (GB); Virginia Ann Wood, Basingstoke (GB); Jeremy Gilmore, Basingstoke (GB)

(73) Assignee: Eli Lilly and Company, Indianapolis, IN (US)

( * ) Notice: Subject to any disclaimer, the term of this patent is extended or adjusted under 35 U.S.C. 154(b) by 121 days.

(21) Appl. No.: 10/558,588

(22) PCT Filed: May 25, 2004

(86) PCT No.: PCT/US2004/014529

§ 371 (c)(1),
(2), (4) Date: Nov. 29, 2005

(87) PCT Pub. No.: WO2005/000305

PCT Pub. Date: Jan. 6, 2005

(65) Prior Publication Data

US 2007/0066663 A1    Mar. 22, 2007

Related U.S. Application Data

(60) Provisional application No. 60/511,045, filed on Oct. 14, 2003.

(30) Foreign Application Priority Data

Jun. 20, 2003    (GB) .................................. 0314414.4

(51) Int. Cl.
| | | |
|---|---|---|
| *A01N 43/90* | (2006.01) | |
| *A01N 43/40* | (2006.01) | |
| *A61K 31/44* | (2006.01) | |
| *A61K 31/445* | (2006.01) | |
| *C07D 453/02* | (2006.01) | |
| *C07D 211/56* | (2006.01) | |
| *C07D 211/98* | (2006.01) | |

(52) U.S. Cl. ....................... 514/305; 514/318; 514/326; 514/329; 546/137; 546/244

(58) Field of Classification Search ................. 546/244, 546/121, 137; 514/299, 315, 318, 326, 329, 514/305
See application file for complete search history.

(56) References Cited

FOREIGN PATENT DOCUMENTS

| FR | 2 321 890 | 3/1977 |
|---|---|---|
| FR | 2321890 | * 3/1977 |
| WO | WO 02/16356 A2 | 2/2002 |
| WO | 03/037271 | * 5/2003 |
| WO | WO 2004/035574 A2 | 4/2004 |

OTHER PUBLICATIONS

Roberts et al., Human Mutation, 2000, vol. 16, pp. 77-85.*
De Costa, et al., "Synthesis and Evaluation of Conformationally Restricted N-[2-(3,4-Dichlorophenyl)ethyl]-N-methyl-2-(1-pyrrolidinyl)ethylamines at σ Receptors. 2. Piperazines, Bicyclic Amines, Bridged Bicyclic Amines, and Miscellaneous Compounds"; Journal of Medicinal Chemical Society, vol. 36, 1993, 2311-2320.
PCT International Search Report.

* cited by examiner

*Primary Examiner*—D. Margaret Seaman
*Assistant Examiner*—Niloofar Rahmani
(74) *Attorney, Agent, or Firm*—Tonya L. Combs; Charles E. Cohen; Thomas E. Jackson

(57) ABSTRACT

The present invention provides compounds of formula (I)

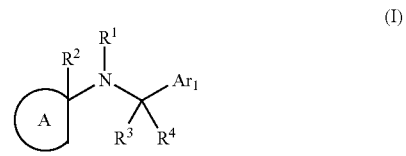

and pharmaceutically acceptable salts thereof, which are useful for the inhibition of the uptake of one or more physiologically active monoamines (serotonin, norepinephrine, and dopamine).

11 Claims, No Drawings

3-AMINOPIPERIDINES AND 3-AMINOQUINUCLIDINES AS INHIBITORS OF MONOAMINE UPTAKE

This is the national phase application, under 35 USC 371, for PCT/US2004/014529, filed 25 May 2004, which claims the benefit GB application 0314414.4, filed 20 Jun. 2003, and U.S. provisional application 60/511,045, filed 14 Oct. 2003.

The present invention is directed to compounds which inhibit the uptake of one or more physiologically active monoamines selected from serotonin (also called 5-hydroxytryptamine or 5-HT), norepinephrine (also called noradrenaline) and dopamine. There is a large body of scientific evidence pointing to the physiological role of these monoamines as neurotransmitters. Consequently, compounds which are capable of inhibiting the uptake of one or more of these monoamines find utility in the treatment of disorders of the central and/or peripheral nervous system.

It is known that the 3-aryloxy-3-substituted-1-aminopropane class of compounds have demonstrated particular diversity in their ability to inhibit the uptake of monoamines. Fluoxetine (N-methyl 3-((4-trifluoromethylphenyl)oxy)-3-phenyl-1-aminopropane hydrochloride), for example, is a selective serotonin uptake inhibitor that has found great market acceptance in the treatment of depression and has also been approved for the treatment of a number of other disorders. Atomoxetine ((−)—N-methyl3-((2-methylphenyl)oxy)-3-phenyl-1-aminopropane hydrochloride), is a selective norepinephrine uptake inhibitor that is approved for the treatment of attention deficit/hyperactivity disorder. Duloxetine ((+)—N-methyl3-(1-naphthalenyloxy)-3-(2-thienyl)-1-aminopropane hydrochloride), is a dual serotonin and norepinephrine uptake inhibitor that is in clinical development for the treatment of depression and stress urinary incontinence.

WO 91/09844 discloses 2-aryl-3-(N-arylmethylamino)piperidines as substance P antagonists.

WO93/01170 discloses another generic class of 3-amino-aza-cycloalkanes/alkenes as substance P antagonists.

WO93/15073 describes azabicyclic compounds as calcium channel antagonists.

WO94/13291 discloses a generic class of cyclic secondary amine derivatives as calcium channel antagonists.

WO02/24649 discloses a generic class of substituted amino-aza-cycloalkanes as inhibitors of the *plasmodium falciparum* protease plasmepsin II or related aspartic proteases.

WO2004/016608 describes certain quinuclidine derivatives that are modulators of the nicotinic and/or of the monoamine receptors.

It would be advantageous to provide further compounds which are capable of inhibiting the uptake of one or more monoamines selected from serotonin, norepinephrine and dopamine. Preferably, such compounds would exhibit one or more of the following characteristics when compared with known monoamine uptake inhibitors—(i) improved potency in their inhibition of one or more of these monoamines, (ii) improved selectivity in their inhibition of one or more of these monoamines, (iii) improved bioavailability, (iv) minimal interaction with metabolic enzymes such as CYP2D6 and (v) improved acid stability.

Accordingly, the present invention provides a compound of formula (I)

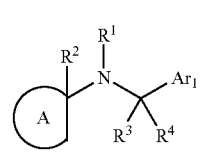

wherein

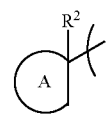

is a group of formula (a) or (b)

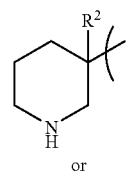

or

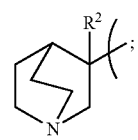

$R^1$ is $C_1$-$C_6$alkyl (optionally substituted with 1, 2 or 3 halo substituents and/or with 1 substituent selected from —S—($C_1$-$C_3$alkyl), —O—($C_1$-$C_3$alkyl) (optionally substituted with 1, 2 or 3 F atoms), —O—($C_3$-$C_6$cycloalkyl), —SO$_2$—($C_1$-$C_3$alkyl), —CN, —COO—($C_1$-$C_2$alkyl) and —OH); $C_2$-$C_6$alkenyl; —(CH$_2$)$_q$—Ar$_2$; or a group of formula (i) or (ii)

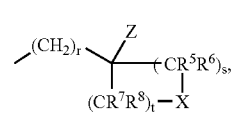

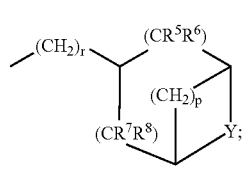

$R^2$, $R^3$ and $R^4$ are each independently selected from hydrogen or $C_1$-$C_2$alkyl;

$R^5$, $R^6$, $R^7$ and $R^8$ are at each occurrence independently selected from hydrogen or $C_1$-$C_2$alkyl;

—X— is a bond, —CH$_2$—, —CH=CH—, —O—, —S—, or —SO$_2$—;
—Y— is a bond, —CH$_2$— or —O—;
-Z is hydrogen, —OH or —O—(C$_1$-C$_3$alkyl);
p is 0, 1 or 2;
q is 0, 1 or 2;
r is 0 or 1;
s is 0, 1, 2 or 3;
t is 0, 1, 2, 3 or 4;
Ar$_1$ is selected from:
(i) a phenyl group or a 5- or 6-membered monocyclic heteroaromatic group each of which is optionally substituted with 1, 2, 3, 4 or 5 substituents (depending on the number of available substitution positions) each independently selected from halo, cyano, C$_1$-C$_4$alkyl (optionally substituted with 1, 2 or 3 F atoms), —O—(C$_1$-C$_4$alkyl) (optionally substituted with 1, 2 or 3 F atoms) and —S—(C$_1$-C$_4$alkyl) (optionally substituted with 1, 2 or 3 F atoms) and/or with 1 substituent selected from pyridinyl, pyrazolyl, phenyl (optionally substituted with 1, 2 or 3 halo substituents), benzyl (optionally substituted with 1, 2 or 3 halo substituents) and phenoxy (optionally substituted with 1, 2 or 3 halo substituents) with the proviso that only C$_1$-C$_4$alkyl may be a substituent for the H of any —NH— moiety present within a 5- or 6-membered monocyclic heteroaromatic group; or
(ii) a naphthyl group or an 8-, 9- or 10-membered bicyclic heteroaromatic group each of which is optionally substituted with 1, 2, 3, 4, 5 or 6 substituents (depending on the number of available substitution positions) each independently selected from halo, cyano, C$_1$-C$_4$alkyl (optionally substituted with 1, 2 or 3 F atoms), —O—(C$_1$-C$_4$alkyl) (optionally substituted with 1, 2 or 3 F atoms) and —S—(C$_1$-C$_4$alkyl) (optionally substituted with 1, 2 or 3 F atoms) with the proviso that only C$_1$-C$_4$alkyl may be a substituent for the H of any —NH— moiety present within an 8-, 9- or 10-membered bicyclic heteroaromatic group; and Ar$_2$ is selected from
(i) a phenyl group or a 5- or 6-membered monocyclic heteroaromatic group each of which is optionally substituted with 1, 2, 3, 4 or 5 substituents (depending on the number of available substitution positions) each independently selected from halo, cyano, C$_1$-C$_4$alkyl (optionally substituted with 1, 2 or 3 F atoms), —O—(C$_1$-C$_4$alkyl) (optionally substituted with 1, 2 or 3 F atoms) and —S—(C$_1$-C$_4$alkyl) (optionally substituted with 1, 2 or 3 F atoms) with the proviso that only C$_1$-C$_4$alkyl may be a substituent for the H of any —NH— moiety present within a 5- or 6-membered monocyclic heteroaromatic group; or
(ii) a naphthyl group or an 8-, 9- or 10-membered bicyclic heteroaromatic group each of which is optionally substituted with 1, 2, 3, 4, 5 or 6 substituents (depending on the number of available substitution positions) each independently selected from halo, cyano, C$_1$-C$_4$alkyl (optionally substituted with 1, 2 or 3 F atoms), —O—(C$_1$-C$_4$alkyl) (optionally substituted with 1, 2 or 3 F atoms) and —S—(C$_1$-C$_4$alkyl) (optionally substituted with 1, 2 or 3 F atoms) with the proviso that only C$_1$-C$_4$alkyl may be a substituent for the H of any —NH— moiety present within an 8-, 9- or 10-membered bicyclic heteroaromatic group;

or a pharmaceutically acceptable salt thereof; provided that
(a) the cyclic portion of the group of formula (i) must contain at least three carbon atoms and not more than seven ring atoms;
(b) when —X— is —CH=CH—, then the cyclic portion of the group of formula (i) must contain at least five carbon atoms; and
(c) when -Z is —OH or —O—(C$_1$-C$_3$alkyl), then —X— is —CH$_2$—; and
(d) when —Y— is —O— then p cannot be 0.

For the avoidance of doubt relating to the term "and/or", when R$^1$ is C$_1$-C$_6$alkyl, it is substituted with 0, 1, 2 or 3 halo substituents and with 0 or 1 substituent selected from —S—(C$_1$-C$_3$alkyl), —O—(C$_1$-C$_3$alkyl) (optionally substituted with 1, 2 or 3 F atoms), —O—(C$_3$-C$_6$ cycloalkyl), —SO$_2$—(C$_1$-C$_3$alkyl), —CN, —COO—(C$_1$-C$_2$alkyl) and —H.

Similarly, when Ar$_1$ is a phenyl group or a 5- or 6-membered monocyclic heteroaromatic group, each is substituted with 0, 1, 2, 3, 4 or 5 substituents (depending on the number of available substitution positions) each independently selected from halo, cyano, C$_1$-C$_4$alkyl (optionally substituted with 1, 2 or 3 F atoms), —O—(C$_1$-C$_4$alkyl) (optionally substituted with 1, 2 or 3 F atoms) and —S—(C$_1$-C$_4$alkyl) (optionally substituted with 1, 2 or 3 F atoms) and with 0 or 1 substituent selected from pyridinyl, pyrazolyl, phenyl (optionally substituted with 1, 2 or 3 halo substituents), benzyl (optionally substituted with 1, 2 or 3 halo substituents) and phenoxy (optionally substituted with 1, 2 or 3 halo substituents) with the proviso that only C$_1$-C$_4$alkyl may be a substituent for the H of any —NH— moiety present within a 5- or 6-membered monocyclic heteroaromatic group.

For the avoidance of doubt, when p=0, the group of formula (ii) becomes

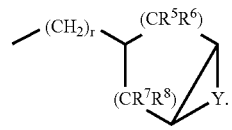

In the present specification the term "C$_1$-C$_6$alkyl" means a monovalent unsubstituted saturated straight-chain or branched-chain hydrocarbon radical having from 1 to 6 carbon atoms.

In the present specification the term "C$_2$-C$_6$alkenyl" means a monovalent unsubstituted unsaturated straight-chain or branched-chain hydrocarbon radical having from 2 to 6 carbon atoms and containing at least one carbon-carbon double bond.

In the present specification the term "C$_3$-C$_6$cycloalkyl" means a monovalent unsubstituted saturated cyclic hydrocarbon radical having from 3 to 6 carbon atoms.

In the present specification the term "C$_1$-C$_6$alkylene" means a divalent unsubstituted saturated straight-chain or branched-chain hydrocarbon radical having from 1 to 6 carbon atoms. This term is not limited to divalent radicals wherein the radical carbon atoms are located at the termini of the hydrocarbon chain, for example

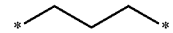

but also include divalent radicals wherein the radical carbon atoms are located within the hydrocarbon chain, for example

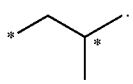

In the present specification the term "halo" or "halogen" means F, Cl, Br or I.

In the present specification the term "$C_1$-$C_4$difluoroalkyl" means a monovalent unsubstituted saturated straight-chain or branched-chain hydrocarbon radical having from 1 to 4 carbon atoms wherein two hydrogen atoms are substituted with two fluoro atoms. Preferably the two fluoro atoms are attached to the same carbon atom.

In the present specification the term "$C_1$-$C_4$trifluoroalkyl" means a monovalent unsubstituted saturated straight-chain or branched-chain hydrocarbon radical having from 1 to 4 carbon atoms wherein three hydrogen atoms are substituted with three fluoro atoms. Preferably the three fluoro atoms are attached to the same carbon atom.

In the present specification the term "benzyl" means a monovalent unsubstituted phenyl radical linked to the point of substitution by a —$CH_2$— group.

In the present specification the term "phenoxy" means a monovalent unsubstituted phenyl radical linked to the point of substitution by an O atom.

In the present specification the term "5- or 6-membered monocyclic heteroaromatic group" means a monocyclic aromatic group with a total of 5 or 6 atoms in the ring wherein from 1 to 4 of those atoms are each independently selected from N, O and S. Preferred groups have 1 or 2 atoms in the ring which are each independently selected from N, O and S. Examples of 5-membered monocyclic heteroaromatic groups include pyrrolyl (also called azolyl), furanyl, thienyl, pyrazolyl (also called 1H-pyrazolyl and 1,2-diazolyl), imidazolyl, oxazolyl (also called 1,3-oxazolyl), isoxazolyl (also called 1,2-oxazolyl), thiazolyl (also called 1,3-thiazolyl), isothiazolyl (also called 1,2-thiazolyl), triazolyl, oxadiazolyl, thiadiazolyl, tetrazolyl, oxatriazolyl and thiatriazolyl. Examples of 6-membered monocyclic heteroaromatic groups include pyridinyl, pyrimidyl, pyrazinyl, pyridazinyl and triazinyl.

"Pyrrolyl" as used herein includes pyrrol-1-yl, pyrrol-2-yl and pyrrol-3-yl.

"Furanyl" (also called "furyl") as used herein includes furan-2-yl and furan-3-yl (also called 2-furyl and 3-furyl). Furan-2-yl is preferred.

"Thienyl" (also called "thiophenyl") as used herein includes thien-2-yl and thien-3-yl (also called 2-thiophenyl and 3-thiophenyl).

"Pyrazolyl" as used herein includes pyrazol-1-yl, pyrazol-3-yl, pyrazol-4-yl and pyrazol-5-yl (also called 1-pyrazole, 3-pyrazole, 4-pyrazole and 5-pyrazole). Pyrazol-1-yl is preferred.

"Imidazolyl" as used herein includes imidazol-1-yl, imidazol-2-yl, imidazol-4-yl and imidazol-5-yl.

"Oxazolyl" as used herein includes oxazol-2-yl, oxazol-4-yl and oxazol-5-yl.

"Isoxazolyl" as used herein includes isoxazol-3-yl, isoxazol-4-yl, and isoxazol-5-yl.

"Thiazolyl" as used herein includes thiazol-2-yl, thiazol-4-yl and thiazol-5-yl (also called 2-thiazolyl, 4-thiazolyl and 5-thiazolyl).

"Isothiazolyl" as used herein includes isothiazol-3-yl, isothiazol-4-yl, and isothiazol-5-yl.

"Triazolyl" as used herein includes 1,2,3-triazol-1-yl, 1,2,3-triazol-4-yl, 1,2,3-triazol-5-yl, 1,2,4-triazol-1-yl, 1,2,4-triazol-3-yl and 1,2,4-triazol-5-yl.

"Oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl.

"Thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl.

"Tetrazolyl" as used herein includes tetrazol-1-yl and tetrazol-5-yl.

"Oxatriazolyl" as used herein includes 1,2,3,4-oxatriazol-5-yl and 1,2,3,5-oxatriazol-4-yl.

"Thiatriazolyl" as used herein includes 1,2,3,4-thiatriazol-5-yl and 1,2,3,5-thiatriazol-4-yl.

"Pyridinyl" (also called "pyridyl") as used herein includes pyridin-2-yl, pyridin-3-yl and pyridin-4-yl (also called 2-pyridyl, 3-pyridyl and 4-pyridyl).

"Pyrimidyl" as used herein includes pyrimid-2-yl, pyrimid-4-yl, pyrimid-5-yl and pyrimid-6-yl.

"Tyridazinyl" as used herein includes pyridazin-3-yl and pyridazin-4-yl.

"Pyrazinyl" as used herein includes pyrazin-2-yl and pyrazin-3-yl.

"Triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl.

In the present specification the term "8-, 9- or 10-membered bicyclic heteroaromatic group" means a fused bicyclic aromatic group with a total of 8, 9 or 10 atoms in the ring system wherein from 1 to 4 of those atoms are each independently selected from N, O and S. Preferred groups have from 1 to 3 atoms in the ring system which are each independently selected from N, O and S. Suitable 8-membered bicyclic heteroaromatic groups include imidazo[2,1-b][1,3]thiazolyl, thieno[3,2-b]thienyl, thieno[2,3-d][1,3]thiazolyl and thieno[2,3-d]imidazolyl. Suitable 9-membered bicyclic heteroaromatic groups include indolyl, isoindolyl, benzofuranyl (also called benzo[b]furanyl), isobenzofuranyl (also called benzo[c]furanyl), benzothienyl (also called benzo[b]thienyl), isobenzothienyl (also called benzo[c]thienyl), indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-beizothiadiazolyl, thienopyridinyl, purinyl and imidazo[1,2-a]pyridine. Suitable 10-membered bicyclic heteroaromatic groups include quinolinyl, isoquinolinyl, cinnolinyl, quinazolinyl, quinoxalinyl, 1,5-naphthyridyl, 1,6-naphthyridyl, 1,7-naphthyridyl and 1,8-naphthyridyl.

"Imidazo[2,1-b][1,3]thiazolyl" as used herein includes imidazo[2,1-b][1,3]thiazol-2-yl, imidazo[2,1-b][1,3]thiazol-3-yl, imidazo[2,1-b][1,3]thiazol-5-yl and imidazo[2,1-b][1,3]thiazol-6-yl.

"Thieno[3,2-b]thienyl" as used herein includes thieno[3,2-b]thien-2-yl, thieno[3,2-b]thien-3-yl, thieno[3,2-b]thien-5-yl and thieno[3,2-b]thien-6-yl.

"Thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl.

"Thieno[2,3-d]imidazolyl" as used herein includes thieno[2,3-d]imidazol-2-yl, thieno[2,3-d]imidazol-4-yl and thieno[2,3-d]imidazol-5-yl.

"Indolyl" as used herein includes indol-1-yl, indol-2-yl, indol-3-yl, indol-4-yl, indol-5-yl, indol-6-yl and indol-7-yl.

"Isoindolyl" as used herein includes isoindol-1-yl, isoindol-2-yl, isoindol-3-yl, isoindol-4-yl, isoindol-5-yl, isoindol-6-yl and isoindol-7-yl.

"Benzofuranyl" as used herein includes benzofuran-2-yl, benzofuran-3-yl, benzofuran-4-yl, benzofuran-5-yl, benzofuran-6-yl and benzofuran-7-yl.

"Isobenzofuranyl" as used herein includes isobenzofuran-1-yl, isobenzofuran-3-yl, isobenzofuran-4-yl, isobenzofuran-5-yl, isobenzofuran-6-yl and isobenzofuran-7-yl.

"Benzothienyl" (also called "benzothiophenyl") as used herein includes benzothien-2-yl, benzothien-3-yl, benzothien-4-yl, benzothien-5-yl, benzothien-6-yl and benzothien-7-yl (also called 2-benzo[b]thiophenyl, 3-benzo[b]thiophenyl, 4-benzo[b]thiophenyl, 5-benzo[b]thiophenyl, 6-benzo[b]thiophenyl and 7-benzo[b]thiophenyl).

"Isobenzothienyl" as used herein includes isobenzothien-1-yl, isobenzothien-3-yl, isobenzothien-4-yl, isobenzothien-5-yl, isobenzothien-6-yl and isobenzothien-7-yl.

"Indazolyl" as used herein includes indazol-1-yl, indazol-3-yl, indazol-4-yl, indazol-5-yl, indazol-6-yl and indazol-7-yl.

"Benzimidazolyl" as used herein includes benzimidazol-1-yl, benzimidazol-2-yl, benzimidazol-4-yl, benzimidazol-5-yl, benzimidazol-6-yl and benzimidazol-7-yl.

"1,3-Benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl.

"1,2-Benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl.

"2,1-Benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl.

"1,3-Benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl.

"1,2-Benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl.

"2,1-Benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl.

"Benzotriazolyl" as used herein includes benzotriazol-1-yl, benzotriazol-4-yl, benzotriazol-5-yl, benzotriazol-6-yl and benzotriazol-7-yl.

"1,2,3-Benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl.

"2,1,3-Benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl.

"1,2,3-Benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl.

"2,1,3-Benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl.

"Thienopyridinyl" as used herein includes thieno[2,3-b]pyridinyl, thieno[2,3-c]pyridinyl, thieno[3,2-c]pyridinyl and thieno[3,2-b]pyridinyl.

"Purinyl" as used herein includes purin-2-yl, purin-6-yl, purin-7-yl and purin-8-yl.

"Imidazo[1,2-a]pyridinyl" as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl.

"Quinolinyl" as used herein includes quinolin-2-yl, quinolin-3-yl, quinolin-4-yl, quinolin-5-yl, quinolin-6-yl, quinolin-7-yl and quinolin-8-yl.

"Isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl.

"Cinnolinyl" as used herein includes cinnolin-3-yl, cinnolin-4-yl, cinnolin-5-yl, cinnolin-6-yl, cinnolin-7-yl and cinnolin-8-yl.

"Quinazolinyl" as used herein includes quinazolin-2-yl, quinazolin-4-yl, quinazolin-5-yl, quinazolin-6-yl, quinazolin-7-yl and quinazolin-8-yl.

"1,4-Naphthyridyl" as used herein includes 1,4-naphthyrid-2-yl, 1,4-naphthyrid-3-yl, 1,4-naphthyrid-5-yl, 1,4-naphthyrid-6-yl, 1,4-naphthyrid-7-yl and 1,4-naphthyrid-8-yl.

"1,5-Naphthyridyl" as used herein includes 1,5-naphthyrid-2-yl, 1,5-naphthyrid-3-yl, 1,5-naphthyrid-4-yl, 1,5-naphthyrid-6-yl, 1,5-naphthyrid-7-yl and 1,5-naphthyrid-8-yl.

"1,6-Naphthyridyl" as used herein includes 1,6-naphthyrid-2-yl, 1,6-naphthyrid-3-yl, 1,6-naphthyrid-4-yl, 1,6-naphthyrid-5-yl, 1,6-naphthyrid-7-yl and 1,6-naphthyrid-8-yl.

"1,7-Naphthyridyl" as used herein includes 1,7-naphthyrid-2-yl, 1,7-naphthyrid-3-yl, 1,7-naphthyrid-4-yl, 1,7-naphthyrid-5-yl, 1,7-naphthyrid-6-yl and 1,7-naphthyrid-8-yl.

"1,8-Naphthyridyl" as used herein includes 1,8-naphthyrid-2-yl, 1,8-naphthyrid-3-yl, 1,8-naphthyrid-4-yl, 1,8-naphthyrid-5-yl, 1,8-naphthyrid-6-yl and 1,8-naphthyrid-7-yl.

In the present specification the term "naphthyl" includes 1-naphthyl, and 2-naphthyl. 1-naphthyl is preferred.

In the above definitions, similar terms specifying different numbers of C atoms take an analogous meaning. For example the terms "$C_1$-$C_4$alkyl" and "$C_1$-$C_3$alkyl" mean a monovalent unsubstituted saturated straight-chain or branched-chain hydrocarbon radical having from 1 to 4 and 1 to 3 carbon atoms respectively. The term "$C_1$-$C_4$alkyl" includes methyl, ethyl, n-propyl, iso-propyl, n-butyl, iso-butyl, sec-butyl, and tert-butyl. The term "$C_1$-$C_3$alkyl" includes methyl, ethyl, n-propyl and iso-propyl.

It will be appreciated that when s is 2 or 3, then each $R^5$ and/or each $R^6$ can be different. In the same way when t is 2 or 3, then each $R^7$ and/or each $R^8$ can be different.

In a preferred embodiment of the present invention, $Ar_1$ is phenyl, pyridyl, thiazolyl, benzothiophenyl or naphthyl; wherein said phenyl, pyridyl or thiazolyl group may be substituted with 1, 2 or 3 substituents each independently selected from halo, cyano, $C_1$-$C_4$alkyl (optionally substituted with 1, 2 or 3 F atoms), —O—($C_1$-$C_4$alkyl) (optionally substituted with 1, 2 or 3 F atoms) and —S—($C_1$-$C_4$alkyl) (optionally substituted with 1, 2 or 3 F atoms) and/or with 1 substituent selected from pyridyl, pyrazole, phenyl (optionally substituted with 1, 2 or 3 halo substituents), benzyl and phenoxy (optionally substituted with 1, 2 or 3 halo substituents); and wherein said benzothiophenyl or naphthyl group may be optionally substituted with 1, 2 or 3 substituents each independently selected from halo, cyano, $C_1$-$C_4$alkyl (optionally substituted with 1, 2 or 3 F atoms), —O—($C_1$-$C_4$alkyl) (optionally substituted with 1, 2 or 3 F atoms), and —S—($C_1$-$C_4$alkyl) (optionally substituted with 1, 2 or 3 F atoms); and $Ar_2$ is naphthyl, pyridyl, thiazolyl, furyl, thiophenyl, benzothiophenyl, or phenyl, wherein said naphthyl, pyridyl, thiazolyl, furyl, thiophenyl, benzothiophenyl, or phenyl may be substituted with 1, 2 or 3 substituents each independently selected from halo, $C_1$-$C_4$alkyl (optionally substituted with 1, 2 or 3 F atoms) and —O—($C_1$-$C_4$alkyl) (optionally substituted with 1, 2 or 3 F atoms).

In a preferred embodiment of the present invention, when R1 is a group of formula (i) and is 0, Z is H.

A particular embodiment of the present invention is a compound of formula (I')

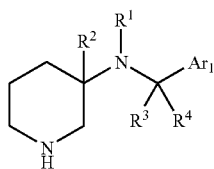

wherein $R^1$, $R^2$, $R^3$, $R^4$ and $Ar_1$ have the values defined in formula (I) above.

Another particular embodiment of the present invention is a compound of formula (I")

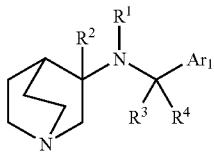

wherein $R^1$, $R^2$, $R^3$, $R^4$ and $Ar_1$ have the values defined in formula (I) above.

In a preferred embodiment of the present invention $R^1$ is $C_1$-$C_6$alkyl, $C_2$-$C_6$alkenyl, —$(CH_2)_m$—$CF_3$, —$(CH_2)$, —S—($C_1$-$C_3$alkyl), —$CH_2$—COO—($C_1$-$C_2$alkyl), —($C_1$-$C_5$alkylene)-O—($C_1$-$C_3$alkyl), —($C_1$-$C_5$alkylene)-O—($C_3$-$C_6$cycloalkyl), —($C_1$-$C_5$alkylene)-$SO_2$—($C_1$-$C_3$alkyl), —($C_1$-$C_5$alkylene)-$OCF_3$, —($C_1$-$C_6$alkylene)-OH, —($C_1$-$C_5$alkylene)-CN, —$(CH_2)_q$—$Ar_2$ or a group of formula (ia), (ib) or (ii)

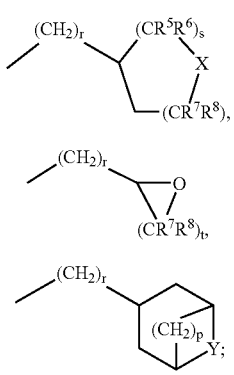

$R^2$, $R^3$, $R^4$, $R^5$, $R^6$, $R^7$, $R^8$, —X—, —Y—, p, q, r and s have the values defined above;
m is 1, 2 or 3;
n is 1, 2 or 3;
t is 2, 3 or 4;
—$Ar_1$ is phenyl, pyridyl, thiazolyl or naphthyl; wherein said phenyl, pyridyl or thiazolyl group may be substituted with 1, 2 or 3 substituents each independently selected from halo, trifluoromethyl, cyano, $C_1$-$C_4$alkyl, —O—($C_1$-$C_4$alkyl), —O—($C_1$-$C_4$difluoroalkyl), —O—($C_1$-$C_4$trifluoroalkyl), —S—($C_1$-$C_4$alkyl), —S—($C_1$-$C_2$trifluoroalkyl) and/or with 1 substituent selected from pyridyl, pyrazole, phenyl (optionally substituted with 1, 2 or 3 halo substituents) and phenoxy (optionally substituted with 1, 2 or 3 halo substituents); and wherein said naphthyl group may be optionally substituted with 1, 2 or 3 substituents each independently selected from halo, trifluoromethyl, cyano, $C_1$-$C_4$alkyl, —O—($C_1$-$C_4$alkyl), —O—($C_1$-$C_4$difluoroalkyl), —O—($C_1$-$C_4$trifluoroalkyl), —S—($C_1$-$C_4$alkyl), —S—($C_1$-$C_2$trifluoroalkyl);

$Ar_2$ is naphthyl, pyridyl, thiazolyl, furyl, thiophenyl, benzothiophenyl, or phenyl, wherein said naphthyl, pyridyl, thiazolyl, furyl, thiophenyl, benzothiophenyl, or phenyl may be substituted with 1, 2 or 3 substituents each independently selected from halo, $C_1$-$C_4$alkyl, trifluoromethyl and —O—($C_1$-$C_4$alkyl).

In a preferred embodiment of the present invention $R^2$ is hydrogen. In another preferred embodiment of the present invention $R^3$ and $R^4$ are hydrogen. More preferably $R^2$, $R^3$ and $R^4$ are hydrogen.

In a preferred embodiment of the present invention each $R^5$ and $R^6$ is hydrogen. In another preferred embodiment of the present invention each $R^7$ and $R^8$ is hydrogen. More preferably $R^5$, $R^6$, $R^7$ and $R^8$ are hydrogen.

In a preferred embodiment of the present invention $R^1$ is $C_1$-$C_6$alkyl. More preferably $R^1$ is n-propyl, 1-methylethyl (i-propyl), 2-methylpropyl (i-butyl), 2-methylbutyl, 2,2-dimethylbutyl.

In another preferred embodiment of the present invention $R^1$ is —($C_4$-$C_5$alkylene)-OH. More preferably $R^1$ is 2,2-dimethyl-2-hydroxyethyl or 3,3-dimethyl-3-hydroxypropyl.

In another preferred embodiment of the present invention $R^1$ is a group of formula (i) and each $R^5$ and $R^6$ is hydrogen. More preferably each $R^5$, $R^6$, $R^7$ and $R^8$ is hydrogen.

In another preferred embodiment of the present invention $R^1$ is a group of formula (ii) and each $R^5$ and $R^6$ is hydrogen. More preferably each $R^5$, $R^6$, $R^7$ and $R^8$ is hydrogen.

In another preferred embodiment of the present invention $R^1$ is a group of formula (i), r is 0 or 1, s is 2, t is 1 or 2, -Z is hydrogen and —X— is —O—, —S— or —$SO_2$—. More preferably $R^1$ is a group of formula (i), r is 0 or 1, s is 2, t is 1 or 2, -Z is hydrogen and —X— is —O—, for example tetrahydro-2H-pyran-4-yl, tetrahydrofuran-3-yl or (tetrahydrofuran-3-yl)methyl. Most preferably $R^1$ is a group of formula (i), r is 0, s is 2, t is 1 or 2, -Z is hydrogen and —X— is —O—, for example tetrahydro-2H-pyran-4-yl or tetrahydrofuran-3-yl.

In another preferred embodiment of the present invention $R^1$ is a group of formula (i), r is 0, s is 1, 2 or 3, t is 1, -Z is hydrogen and —X— is $CH_2$—, for example cyclobutyl, cyclopentyl or cyclohexyl.

In another preferred embodiment of the present invention $R^1$ is a group of formula (i), r is 1, s is 0, 1, 2 or 3, t is 1, -Z is hydrogen and —X— is $CH_2$—.

In another preferred embodiment of the present invention $R^1$ is a group of the formula (ia). More preferably $R^1$ is a group of the formula (ia) and each $R^5$, $R^6$, $R^7$ and $R^8$ is hydrogen.

In another preferred embodiment of the present invention $R^1$ is a group of the formula (ib). More preferably $R^1$ is a group of the formula (ib), r is 1, t is 3, and each $R^7$ and $R^8$ is hydrogen.

In another preferred embodiment of the present invention $R^1$ is —$(CH_2)_m$—$CF_3$. More preferably $R^1$ is —$(CH_2)_m$—$CF_3$ and m is 1, 2, or 3.

In another preferred embodiment of the present invention $R^1$ is —$(CH_2)_n$—S—$(C_1$-$C_3$alkyl).

More preferably $R^1$ is —$(CH_2)_3$—S—$CH_3$.

In another preferred embodiment of the present invention $R^1$ is —$CH_2$—COO—$(C_1$-$C_2$alkyl).

More preferably $R^1$ is —$CH_2$—COOCH$_3$.

In another preferred embodiment of the present invention $R^1$ is —$(C_1$-$C_5$alkylene)-O—$(C_1$-$C_3$alkyl). More preferably $R^1$ is —$(C_3$-$C_4$alkylene)-OCH$_3$.

In another preferred embodiment of the present invention $R^1$ is —$(C_1$-$C_5$alkylene)-O—$(C_3$-$C_6$cycloalkyl). More preferably $R^1$ is —$CH_2$—$CH_2$—O-cyclobutyl.

In another preferred embodiment of the present invention $R^1$ is —$(C_1$-$C_5$alkylene)-SO$_2$—$(C_1$-$C_3$alkyl).

In another preferred embodiment of the present invention $R^1$ is —$(C_1$-$C_5$alkylene)-OCF$_3$.

More preferably $R^1$ is —$CH_2$—$CH_2$—OCF$_3$.

In another preferred embodiment of the present invention $R^1$ is —$(C_1$-$C_5$alkylene)-CN.

More preferably $R^1$ is —$(C_2$-$C_4$alkylene)-CN. Most preferably —$CH_2$—$CH_2$—CN or —$CH_2$—$C(CH_3)_2$—CN.

In another preferred embodiment of the present invention $R^1$ is —$(CH_2)_q$—Ar$_2$, and q is 1. More preferably $R^1$ is —$(CH_2)_q$—Ar$_2$, q is 1 and —Ar$_2$ is pyridyl, phenyl or phenyl substituted with 1, 2 or 3 substituents each independently selected from halo, trifluoromethyl, $C_1$-$C_4$ alkyl or O—$(C_1$-$C_4$alkyl).

In another preferred embodiment of the present invention —Ar$_1$ is phenyl; phenyl substituted with 1, 2 or 3 substituents each independently selected from halo, trifluoromethyl and $C_1$-$C_4$alkyl and/or with 1 substituent selected from phenyl, phenyl-substituted with 1, 2 or 3 halo substituents, pyridyl, pyrazole, phenoxy and phenoxy substituted with 1, 2 or 3 halo substituents; pyridyl; or pyridyl substituted with 1, 2 or 3 substituents each independently selected from halo, trifluoromethyl and $C_1$-$C_4$alkyl and/or with 1 substituent selected from phenyl and phenyl substituted with 1, 2 or 3 halo substituents. More preferably —Ar$_1$ is phenyl or phenyl substituted with 1, 2 or 3 substituents each independently selected from halo, trifluoromethyl and $C_1$-$C_4$alkyl and/or with 1 substituent selected from phenyl, phenyl substituted with 1, 2 or 3 halo substituents, pyridyl, pyrazole, phenoxy and phenoxy substituted with 1, 2 or 3 halo substituents. Most preferably —Ar$_1$ is phenyl substituted with 1 or 2 substituents each independently selected from halo, trifluoromethyl and $C_1$-$C_4$alkyl and/or with 1 substituent selected from phenyl, phenyl substituted with 1, 2 or 3 halo substituents, pyridyl, pyrazole, phenoxy and phenoxy substituted with 1, 2 or 3 halo substituents. Suitable —Ar$_1$ groups include, for example, 2-methylthiophenyl, 2-methylphenyl, 2-fluorophenyl, 2-chlorophenyl, 2-isopropoxyphenyl, 2-trifluoromethylphenyl, 2-difluoromethoxyphenyl, 2-methoxyphenyl, 2-ethoxyphenyl, 2-(1,1'-biphenyl), 2-phenoxyphenyl, 2-benzylphenyl, 3-trifluoromethoxyphenyl, 3-chlorophenyl, 3-trifluoromethylphenyl, 3-methylphenyl, 3-trifluorothiomethoxyphenyl, 3-methoxyphenyl, 4-trifluoromethylphenyl, 4-chlorophenyl, 4-fluorophenyl, 3,5-dichlorophenyl, 3,5-dimethylphenyl, 3-trifluoromethyl-5-fluorophenyl, 3,5-difluorophenyl, 2,3-dichlorophenyl, 2,3-dimethylphenyl, 2-chloro-3-trifluoromethylphenyl, 2-chloro-3-methylphenyl, 2-methyl-3-chlorophenyl, 2,4-dichlorophenyl, 2,4-dimethyl, 2,4-difluorophenyl, 2-chloro-4-fluorophenyl, 2-trifluoromethyl-4-fluorophenyl, 2-fluoro-4-trifluoromethylphenyl, 2-methyl-4-chlorophenyl, 2-methoxy-4-methylphenyl, 2-trifluoromethyl-5-fluorophenyl, 2,5-dimethylphenyl, 4-fluoro-[1,1'-biphenyl]-2-yl, 2-chloro-5-fluorophenyl, 2-(trifluoromethyl)-6-fluorophenyl, 2-chloro-6-fluorophenyl, 3,4-dichlorophenyl, and 3-chloro-4-fluorophenyl. In general when —Ar$_1$ is phenyl substituted with pyridyl, 3-pyridyl is preferred.

In another preferred embodiment of the present invention —Ar$_1$ is pyridyl or pyridyl substituted with 1, 2 or 3 substituents each independently selected from halo, trifluoromethyl and $C_1$-$C_4$alkyl and/or with 1 substituent selected from phenyl and phenyl substituted with 1, 2 or 3 halo substituents. More preferably —Ar$_1$ is pyridyl substituted with 1 or 2 substituents each independently selected from halo, trifluoromethyl and $C_1$-$C_4$alkyl and/or with 1 substituent selected from phenyl and phenyl substituted with 1, 2 or 3 halo substituents. Suitable —Ar$_1$ groups include, for example, 3-phenyl-2-pyridyl. In general when —Ar$_1$ is a substituted pyridyl, substituted 2-pyridyl is preferred.

Illustrative of the present invention are the compounds identified below or their pharmaceutically acceptable salts:

(3S)—N-(2-Methylpropyl)-N-{[2-(trifluoromethyl)-phenyl]methyl}piperidin-3-amine, (3S)—N-(3,3-Dimethylbutyl)-N-{[2-(trifluoromethyl)-phenyl]methyl}piperidin-3-amine, (3S)—N-Cyclohexyl-N-{[2-(trifluoromethyl)phenyl]-methyl}piperidin-3-amine, (3S)—N-{[5-Fluoro-2-(trifluoromethyl)phenyl]methyl}-N-tetrahydro-2H-pyran-4-ylpiperidin-3-amine, (3S)—N-[(2-Chloro-5-fluorophenyl)methyl]-N-tetrahydro-2H-pyran-4-ylpiperidin-3-amine, (3S)—N-([1,1'-Biphenyl]-2-ylmethyl)-N-tetrahydro-2H-pyran-4-ylpiperidin-3-amine, (3S)—N-[(2-Chlorophenyl)methyl]-N-tetrahydro-2H-pyran-4-ylpiperidin-3-amine, (3S)—N-Tetrahydro-2H-pyran-4-yl-N-{[2-(trifluoromethyl)phenyl]methyl}piperidin-3-amine, (3S)—N-Cyclopentyl-N-{[2-(trifluoromethyl)phenyl]-methyl}piperidin-3-amine, (3S)—N-([1,1'-Biphenyl]-2-ylmethyl)-N-cyclopentyl-piperidin-3-amine, (3S)—N-Cyclopentyl-N-([5-fluoro-1,1'-biphenyl]-2-ylmethyl)-piperidin-3-amine, (3S)—N-(Tetrahydrofuran-3-ylmethyl)-N-{[2-(trifluoromethyl)phenyl]methyl}piperidin-3-amine, N-{[2-(Methyloxy)phenyl]methyl}-N-{[2-(trifluoromethyl)phenyl]methyl}piperidin-3-amine, N-Cyclohexyl-N-{[2-(trifluoromethyl)phenyl]methyl}-piperidin-3-amine, N-(Phenylmethyl)-N-{[2-(trifluoromethyl)phenyl]-methyl}piperidin-3-amine, (3S)—N-(2-Methylpropyl)-N-{[2-(trifluoromethyl)phenyl]-methyl}-1-azabicyclo[2.2.2]octan-3-amine, (3S)—N-([1,1'-Biphenyl]-2-ylmethyl)-N-(2-methylpropyl)-1-azabicyclo[2.2.2]octan-3-amine, (3S)—N-[(3,5-Dichlorophenyl)methyl]-N-(2-methylpropyl)-1-azabicyclo[2.2.2]octan-3-amine, (3S)—N-[(2,4-Dichlorophenyl)methyl]-N-(2-methylpropyl)-1-azabicyclo[2.2.2]octan-3-amine, (3S)—N-{[4-Fluoro-2-(trifluoromethyl)phenyl]methyl}-N-(2-methylpropyl)-1-azabicyclo[2.2.2]octan-3-amine, and (3S)—N-[(4-Fluoro[1,1'-biphenyl]-2-yl)methyl]-N-(2-methylpropyl)-1-azabicyclo[2.2.2]octan-3-amine.

The present invention includes pharmaceutically acceptable salts of the compounds of formula (I). Suitable salts include acid addition salts, including salts formed with inorganic acids (for example hydrochloric, hydrobromic, nitric, sulphuric or phosphoric acid) or with organic acids, such as organic carboxylic acids (for example acetic, fumaric, pyruvic, lactobionic, glycolic, oxalic, maleic, hydroxymaleic, malic, citric, salicylic, o-acetoxybenzoic or tartaric acid), or organic sulphonic acids (for example toluene-p-sulphonic, naphthalenesulfonic, bisethanesulphonic or methanesulphonic acid). Particularly preferred are salts formed with phosphoric, fumaric, L-tartaric, D-tartaric or naphthalenesulfonic acid. Most preferred are salts formed with L-tartaric or D-tartaric acid.

It will be appreciated that certain compounds of formula (I) may possess one or more chiral centres. Where a structural formula does not specify the stereochemistry at one or more chiral centres, it encompasses all possible stereoisomers and all possible mixtures of stereoisomers (including, but not limited to, racemic mixtures), which may result from stereoisomerism at each of the one or more chiral centers. For example, the carbon atom at the three position of the piperidine ring of compounds of formula (I') can give rise to two enantiomers of formulae (Ia) and (Ib):

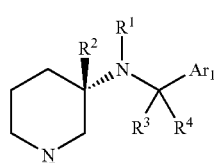

(Ia)

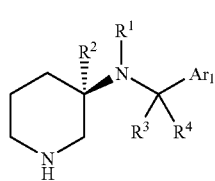

(Ib)

wherein $R^1$, $R^2$, $R^3$, $R^4$ and $Ar_1$ have the values defined in formula (I) above. Said isomers are also an aspect of the present invention. Preferred compounds of the invention are those of formula (Ia). In the same way, the carbon atom at the three position of the quinuclidine ring of compounds of formula (I") can give rise to two enantiomers of formulae (Ic) and (Id):

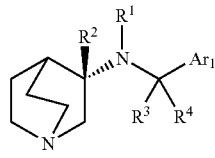

(Ic)

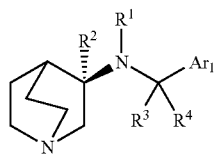

(Id)

wherein $R^1$, $R^2$, $R^3$, $R^4$ and $Ar_1$ have the values defined in formula (I) above. Said isomers are also an aspect of the present invention. Preferred compounds of the invention are those of formula (Ic).

The preferred stereochemistry detailed above also applies to the compounds used as intermediates for the preparation of the compounds of the present invention.

As mentioned above, the compounds of the present invention and their pharmaceutically acceptable salts inhibit the uptake of one or more of the monoamine neurotransmitters serotonin, dopamine and norepinephrine. In view of these properties, the compounds of the present invention and their pharmaceutically acceptable salts are indicated for use in treating disorders which are caused by or linked to decreased neurotransmission of one or more of these monoamines. Such disorders include disorders of the central and/or peripheral nervous system.

One preferred group of compounds of the present invention selectively inhibit the reuptake of serotonin and norepinephrine over dopamine. Preferably said group of compounds of the present invention selectively inhibit the serotonin and norepinephrine transporters relative to the dopamine transporter by a factor of at least five, and even more preferably by a factor of at least ten. Compounds of the present invention with this pharmacological profile are particularly useful for the treatment of depression, eating disorders (including bulimia and anorexia nervosa), inflammatory bowel disorders, functional bowel disorders, dyspepsia, Crohn's disease, iletis, ischemic bowel disease, ulcerative colitis, gastroesophageal reflux for functional bowel disorders, irritable bowel syndrome, obesity, insterstitial cystitis, urethral syndrome, gastric motility disorders, substance abuse (including alcoholism, tobacco abuse, symptoms caused by withdrawal or partial withdrawal from the use of tobacco or nicotine and drug addiction including cocaine abuse), pain (including inflammatory pain, neuropathic pain, non-neuropathic non-inflammatory pain, persistent pain, persistent pain of inflammatory and/or neuropathic origin, headache and migraine), incontinence (including stress urinary incontinence and urge incontinence), dementia of ageing, senile dementia, Alzheimer's, memory loss, Parkinsonism, attention-deficit disorder (including attention-deficit hyperactivity disorder), anxiety, social phobia, disruptive behavior disorders, impulsive control disorders, borderline personality disorder, chronic fatigue syndrome, panic disorders, obsessive compulsive disorder, post-traumatic stress disorder, schizophrenia, gastrointestinal disorders, cardiovascular disorders, hot flushes/flashes, emesis, sleep disorders, cognitive disorders, psychotic disorders, brain trauma, premenstrual syndrome or late luteal syndrome, sexual dysfunction (including premature ejaculation and erectile difficulty), autism, mutism and trichotillomania. They are more particularly useful for the treatment of depression, incontinence (particularly stress urinary incontinence) and pain (particularly persistent pain). They are most particularly useful for the treatment of persistent pain.

For clinical purposes, pain may be divided into two categories: acute pain and persistent pain. Acute pain is provoked by noxious stimulation produced by injury and/or disease of skin, deep somatic structures or viscera, or abnormal function of muscle or viscera that does not produce actual tissue damage. On the other hand, persistent pain can be defined as pain that persists beyond the usual course of an acute disease or a reasonable time for an injury to heal or that is associated with a chronic pathologic process that causes continuous pain or the pain recurs at intervals for months or years. If pain is still present after a cure should have been achieved, it is considered persistent pain. For the purpose of the present invention, persistent pain can be chronic non-remitting or recurrent. The difference in definition between acute and persistent pain is not merely semantic but has an important clinical relevance. For example, a simple fracture of the wrist usually remains painful for a week to 10 days. If the pain is still present beyond the typical course of treatment, it is likely that the patient is developing reflex sympathetic dystrophy, a persistent pain syndrome that requires immediate effective therapy. Early and effective intervention potentially prevents the undue disability and suffering, and avoids the potential development of a condition that becomes refractory to therapy.

Acute and persistent pain differ in etiology, mechanisms, pathophysiology, symptomatology, diagnosis, therapy, and physiological responses. In contrast to the transitory nature of acute pain, persistent pain is caused by chronic pathologic processes in somatic structures or viscera, by prolonged and sometimes permanent dysfunction of the peripheral or central nervous system, or both. Also, persistent pain can sometimes be attributed to psychologic mechanisms and/or environmental factors.

More specifically, persistent pain can be segmented into neuropathic pain (e.g. diabetic neuropathy, infectious neuropathic pain associated with AIDS, non-surgical carpal tunnel syndromes, post-herpetic neuralgia, cervical, thoracic and lumbosacral radiculopathies, stroke-related central pains, trigeminal neuralgia and complex regional pain syndromes I and II), inflammatory pain (e.g. polymyalgia, rheumatoid arthritis and osteoarthritis), and non-neuropathic non-inflammatory pain, non-neuropathic non-inflammatory chronic pain (NNNICP) (e.g. chronic fatigue syndrome, chronic back pain without radiculopathy, fibromyalgia, chronic tension type headaches, inflammatory bowel disorders, irritable bowel syndrome, whiplash injuries, chronic pelvic pain, temporomandibular joint disorder (TMJD) and failed back).

Current therapies for persistent pain include opiates, barbiturate-like drugs such as thiopental sodium and surgical procedures such as neurectomy, rhizotomy, cordotomy, and cordectomy.

Another preferred group of compounds of the present invention selectively inhibit the reuptake of norepinephrine over serotonin and dopamine. Preferably said group of compounds of the present invention selectively inhibit the norepinephrine transporter relative to the serotonin and dopamine transporters by a factor of at least five, and even more preferably by a factor of at least ten. Compounds of the present invention with this pharmacological profile are particularly useful for the treatment of addictive disorder and withdrawal syndrome, an adjustment disorder (including depressed mood, anxiety, mixed anxiety and depressed mood, disturbance of conduct, and mixed disturbance of conduct and mood), an age-associated learning and mental disorder (including Alzheimer's disease), alcohol addiction, anorexia nervosa, apathy, an attention-deficit disorder (ADD) due to general medical conditions, attention-deficit hyperactivity disorder (ADHD) including the predominantly inattentive type of ADHD and the predominantly hyperactive-impulsive type of ADHD, bipolar disorder, bulimia nervosa, chronic fatigue syndrome, chronic or acute stress, cognitive disorders (discussed in more detail below but including mild cognitive impairment (MCI) and cognitive impairment associated with schizophrenia (CIAS)), communication disorders (including stuttering, expressive language disorder, mixed receptive-expressive language disorder, phonological disorder and communication disorder not otherwise specified), conduct disorder, cyclothymic disorder, dementia of the Alzheimers type (DAT), depression (including adolescent depression and minor depression), dysthymic disorder, emotional dysregulation (including emotional dysregulation associated with ADHD, borderline personality disorder, bipolar disorder, schizophrenia, schizoaffective disorder and intermittent explosive disorder), fibromyalgia and other somatoform disorders (including somatization disorder, conversion disorder, pain disorder, hypochondriasis, body dysmorphic disorder, undifferentiated somatoform disorder, and somatoform NOS), generalized anxiety disorder (GAD), hot flashes or vasomotor symptoms, hypotensive states including orthostatic hypotension, impulse control disorders (including intermittent explosive disorder, kleptomania, pyromania, pathological gambling, trichotillomania and impulse-control disorder not otherwise specified), incontinence (i.e., stress incontinence, genuine stress incontinence, and mixed incontinence), an inhalation disorder, an intoxication disorder, learning disabilities (including developmental speech and language disorders (such as developmental articulation disorder, developmental expressive language disorder and developmental receptive language disorder), learning disorders (such as reading disorder, mathematics disorder, disorder of written expression and learning disorder not otherwise specified) and motor skills disorders (such as developmental coordination disorder)), mania, migraine headaches, nicotine addiction, obesity (i.e., reducing the weight of obese or overweight patients), obsessive compulsive disorders and related spectrum disorders, oppositional defiant disorder, pain including chronic pain, neuropathic pain and antinociceptive pain, panic disorder, peripheral neuropathy, post-traumatic stress disorder, personality change due to a general medical condition (including labile type, disinhibited type, aggressive type, apathetic type, paranoid type, combined type and unspecified type), pervasive developmental disorders (including autistic disorder, Asperger's disorder, Rett's disorder, childhood disintegrative disorder, and pervasive developmental disorder not otherwise specified), premenstrual dysphoric disorder (i.e., premenstrual syndrome and late luteal phase dysphoric disorder), psoriasis, a psychoactive substance use disorder, a psychotic disorder (including schizophrenia, schizoaffective and schizophreniform disorders), seasonal affective disorder, selective serotonin reuptake inhibition (SSRI) "poop out" syndrome (i.e., wherein a patient who fails to maintain a satisfactory response to SSRI therapy after an initial period of satisfactory response), a sleep disorder (such as narcolepsy and enuresis), social phobia (including social anxiety disorder), a specific developmental disorder, TIC disorders (e.g., Tourette's Disease), tobacco addiction and vascular dementia. They are most particularly useful for the treatment of ADHD and schizophrenia.

The term "cognitive disorders" (also variously referred to as "cognitive failure," "cognitive insufficiency," "cognitive deficit," "cognitive impairment," "cognitive dysfunction," and the like) refers to the dysfunction, diminution, or loss of one or more cognitive functions, the processes by which knowledge is acquired, retained, and used. Cognitive dysfunction includes cognitive changes associated with ageing ("age-associated memory impairment"), as well as changes due to other causes. Cognitive impairment is most commonly due to a delirium or dementia, but can also occur in association with a number of other medical or neuropsychiatric disorders. More focal cognitive deficits are diagnosed using the criteria disclosed in the *Diagnostic and Statistical Manual of Mental Disorders*, Fourth Edition, Text Revision (DSM-IV-TR™, 2000), American Psychiatric Association, Washington, D.C., as either amnestic disorders (affecting memory) or cognitive disorder not otherwise specified (NOS), which includes executive dysfunction, visuospatial/visuocontructional impairment, attentional deficits, disorientation, etc. These more focal cognitive disorders also have a wide variety of causes, some of which are of unknown etiology.

A delerium is characterized by a disturbance of consciousness with a reduced ability to focus, sustain, or shift attention and a change in cognition that develops over a short period of time. Delirium is very common, and occurs on average in about a fifth of general hospital inpatients, and is even more common in nursing home patients and those with terminal illnesses. The disorders included in the "Delirium" section of the DSM-IV-TR™ are listed according to presumed etiology: Delirium Due to a General Medical Condition, Substance-Induced Delirium (i.e., due to a drug of abuse, a medication, or toxin exposure), Delirium Due to Multiple Etiologies, or Delirium Not Otherwise Specified (if the etiology is indeterminate). As disclosed by Wise et al. ((2002) Delirium (Confusional States), In Wise and Rundell, Eds., *The American Psychiatric Publishing Textbook of Consultation-Liaison Psychiatry, Psychiatry in the Medically Ill*, Second Edition, American Psychiatric Publishing, Inc., Washington, D.C., Chapter 15, pp. 257-272, Table 15-4), exemplary etiological bases of delirium include, but are not limited to, infection, withdrawal from alcohol and drugs, acute metabolic conditions, trauma of various types, CNS pathologies, hypoxia, vitamin deficiencies, endocrinopathies, acute vascular conditions, toxins or drugs, and heavy metals.

A dementia is a chronic condition, usually with a more gradual deterioration of memory and other intellectual functioning and other cognitive skills severe enough to interfere with the ability to perform activities of daily living. Although dementia may occur at any age, it primarily affects the elderly, presenting in more than 15% of persons over 65 years of age and in as many as 40% of persons over 80 years old. Dementia due to Alzheimer's disease is particularly common. Non-Alzheimer's cognitive impairments and/or dementias include, for example, those caused by or associated with: vascular diseases; Parkinson's disease; Lewy body disease (diffuse Lewy body disease); HIV/AIDS; mild cognitive impairments; mild nuerocognitive disorders; age-associated memory impairments; neurologic and/or psychiatric conditions including epilepsy and epilepsy treatments; brain tumors, cysts, lesions, or other inflammatory brain diseases; multiple sclerosis; Down's syndrome; Rett's syndrome; progressive supranuclear palsy; frontal lobe dementia syndromes; schizophrenia and related psychiatric disorders; antipsychotic medications; traumatic brain injury (closed head injury), dementia pugilistica, and other head traumas; normal-pressure hydrocephalus; surgery (including coronary artery by-pass graft surgery) and anaesthesia, electroconvulsive shock therapy, and cancer and cancer therapies.

The dementias are also listed in the "Dementia" section of the DSM-IV-TR™ according to presumed etiology: Dementia of the Alzheimer's Type, Vascular Dementia, Dementia Due to Other General Medical Conditions (e.g., human immunodeficiency virus [HIV] disease, head trauma, Parkinson's disease, Huntington's disease), Substance-Induced Persisting Dementia (i.e., due to a drug of abuse, a medication, or toxin exposure), Dementia Due to Multiple Etiologies, or Dementia Not Otherwise Specified (if the etiology is indeterminate). As disclosed by Gray and Cummings ((2002) Dementia, In Wise and Rundell, Eds., *The American Psychiatric Publishing Textbook of Consultation-Liaison Psychiatry, Psychiatry in the Medically Ill*, Second Edition, American Psychiatric Publishing, Inc., Washington, D.C., Chapter 16, pp. 273-306, Table 16-1), exemplary etiological bases of principal dementia syndromes include, but are not limited to, degenerative disorders (cortical and subcortical), vascular disorders, myelinoclastic disorders, traumatic conditions, neoplastic disorders, hydrocephalic disorders, inflammatory conditions, infections, toxic conditions, metabolic disorders, and psychiatric disorders.

An amnestic disorder is characterized by memory impairment in the absence of other significant accompanying cognitive impairments. The disorders in the "Amnestic Disorders" section of the DSM-IV-TR™ are also listed according to presumed etiology: Amnestic Disorder Due to a General Medical Condition, Substance-Induced Persisting Amnestic Disorder, or Amnestic Disorder Not Otherwise Specified.

Cognitive Disorder Not Otherwise Specified in the DSM-IV-TR™ covers presentations that are characterized by cognitive dysfunction presumed to be due to either a general medical condition or substance use that do not meet criteria for any of the disorders listed elsewhere in the section of the DSM-IV-TR™ entitled "Delirium, Dementia, and Amnestic and Other Cognitive Disorders."

Dementia, amnestic disorders, and cognitive disorders NOS occur in patients with a wide variety of other disorders including, but not limited to, Huntington's disease (chorea); Pick's disease; spinocerebellar ataxias (types 1-11); cortico-basalganglionic degeneration; neuroacanthocytosis; dentatorubropallidoluysian atropy (DRPLA); systemic lupus erythematosus; heavy metal intoxication; alcoholic dementia (Wernicke's encephalopathy); fetal alcohol syndrome; single or multiples strokes, including small vessels (Binswanger's dementia: subcortical arteriosclerotic encephalopathy) and large vessels (multi-infarct dementia); anoxic encephalopathy; tumors; birth anoxia; premature birth; inborn errors of metabolism; neurofibromatosis (Type I); tuberous sclerosis; Hallervorden Spatz disease; Wilson's disease; post-infectious sequelae (e.g., tuberculosis, viral encephalitis, bacterial meningitis); subdural hematoma; subcortical dementia; Creutzfeldt-Jakob disease; Gerstmann-Sträussler-Scheirker disease; general paresis; and syphilis.

As discussed in detail above, cognitive failure may present in patients suffering from a number of disorders, including dementia or delirium, or due to a wide variety of other causes. The compounds of the present invention are useful for the treatment or prevention of cognitive failure associated with, or due to, the disorders or etiologies discussed above, including disorders formally classified in the DSM-IV-TR™. For the convenience of the reader, the DSM-IV-TR™ code numbers or descriptions are supplied below. "ICD-9-CM codes" refers to codes for, e.g., selected general medical conditions and medication-induced disorders contained in the *International Classification of Diseases*, $9^{th}$ Revision, Clinical Modification.

| | |
|---|---|
| Delirium Due to a General Medical Condition | 293.0 |
| Substance-Induced Delirium, including: | |
| Substance Intoxication Delirium: | |
| Code [Specific Substance] Intoxication Delirium: | |
| (291.0 Alcohol; 292.81 Amphetamine [or Amphetamine-Like Substance]; 292.81 | |
| Cannabis; 292.81 Cocaine; 292.81 Hallucinogen; 292.81 Inhalant; 292.81 Opioid; | |
| 292.81 Phencyclidine [or Phencyclidine-Like Substance]; 292.81 Sedative, | |

-continued

| | |
|---|---|
| Hypnotic, or Anxiolytic; 292.81 Other [or Unknown] Substance [e.g., cimetidine, digitalis, benztropine]) | |
| Substance Withdrawal Delirium: | |
| Code [Specific Substance] Withdrawal Delirium: | |
| (291.0 Alcohol; 292.81 Sedative, Hypnotic, or Anxiolytic; 292.81 Other [or Unknown] Substance) | |
| Delirium Due to Multiple Etiologies: | |
| Multiple codes are used, reflecting the specific delirium and specific etiologies, e.g., 293.0 Delirium Due to Viral Encephalitis; 291.0 Alcohol Withdrawal Delirium | |
| Delirium Not Otherwise Specified | 780.09 |
| Dementia of the Alzheimer's Type | 294.1x* (*ICD-9-CM code) |
| Subtypes: | |
| With Early Onset (onset of the dementia is age 65 years or under) | |
| With Late Onset (onset of the dementia is after age 65 years) | |
| Without Behavioral Disturbance | 294.10 |
| With Behavorial Disturbance | 294.11 |
| Vascular Dementia | 290.4x |
| Subtypes: | |
| With Delirium | 290.41 |
| With Delusions | 290.42 |
| With Depressed Mood | 290.43 |
| With Behavioral Disturbance | Uncoded |
| Uncomplicated | 290.40 |
| Dementia Due to HIV Disease | 294.1x* (*ICD-9-CM code) |
| Dementia Due to Head Trauma | 294.1x* (*ICD-9-CM code) |
| Dementia Due to Parkinson's Disease | 294.1x* (*ICD-9-CM code) |
| Dementia Due to Huntington's Disease | 294.1x* (*ICD-9-CM code) |
| Dementia Due to Pick's Disease | 290.1x* (*ICD-9-CM code) |
| Dementia Due to Creutzfeldt-Jakob Disease | 290.1x* (*ICD-9-CM code) |
| Dementia Due to Other General Medical Conditions | 294.1x* (*ICD-9-CM code) |
| Code based on presence or absence of a clinically significant behavioral disturbance: | |
| Without Behavioral Disturbance | 294.10 |
| With Behavioral Disturbance | 294.11 |
| Substance-Induced Persisting Dementia | |
| Code [Specific Substance]-Induced Persisting Dementia: | |
| (291.2 Alcohol; 292.82 Inhalant; 292.82 Sedative, Hypnotic, or Anxiolytic; 292.82 Other [or Unknown] Substance) | |
| Dementia Due to Multiple Etiologies | |
| Coding note: Use multiple codes based on specific dementias and specific etiologies, e.g., 294.10 Dementia of the Alzheimer's Type, With Late Onset, Without Behavioral Disturbance; 290.40 Vascular Dementia, Uncomplicated. | |
| Dementia Not Otherwise Specified | 294.8 |
| Amnestic Disorder Due to a General Medical Condition | 294.0 |
| Transient or Chronic | |
| Substance-Induced Persisting Amnestic Disorder | |
| Code [Specific Substance]-Induced Persisting Amnestic Disorder: | |
| 291.1 Alcohol; 292.83 Sedative, Hypnotic, or Anxiolytic; 292.83 Other [or Unknown] Substance | |
| Amnestic Disorder Not Otherwise Specified | 294.8 |
| Cognitive Disorder Not Otherwise Specified | 294.9 |
| Age-Related Cognitive Decline | 780.9 |

Examples of cognitive disorders due to various etiologies, or associated with various disorders, of particular interest that can be prevented or treated using the compounds of the present invention include: enhancing cognitive functions and executive functioning (ability to plan, initiate, organize, carry out, monitor, and correct one's own behavior) in normal subjects or in subjects exhibiting cognitive dysfunction; treatment of cognitive and attentional deficits associated with prenatal exposure to substances of abuse including, but not limited to, nicotine, alcohol, methamphetamine, cocaine, and heroin; treatment of cognitive impairment caused by chronic alcohol and drug abuse (substance-induced persisting dementia), medicament side effects, and treatment of drug craving and withdrawal; treatment of cognitive deficits in Down's Syndrome patients; treatment of deficits in normal memory functioning comorbid with major depressive and bipolar disorders; treatment of cognitive impairment associated with depression, mental retardation, bipolar disorder, or schizophrenia; treatment of dementia syndromes associated with mania, conversion disorder, and malingering; treatment of problems of attention, prefrontal executive function, or memory due to head trauma or stroke; treatment of cognitive dysfunction in menopausal and post-menopausal women and in women undergoing hormone replacement therapy; treatment of cognitive deficits and fatigue due to, or associated with, cancer and cancer therapies (cognitive deficits are associated with a variety of cancer treatments, including cranial radiation, conventional (standard-dose) chemotherapy, high-dose chemotherapy and hematopoietic (bone-marrow) transplantation, and biologic agents).

Compounds which selectively inhibit the reuptake of norepinephrine over serotonin and dopamine are also useful in a method for treating a patient suffering from or susceptible to psychosis, comprising administering to said patient an effective amount of a first component which is an antipsychotic, in combination with an effective amount of a second component which is a compound of formula (I) that selectively inhibits the reuptake of norepinephrine over serotonin and dopamine. The invention also provides a pharmaceutical composition which comprises a first component that is an antipsychotic, and a second component that is a compound of formula (I) that selectively inhibits the reuptake of norepinephrine over serotonin and dopamine. In the general expressions of this aspect of the present invention, the first component is a compound that acts as an antipsychotic. The antipsychotic may be either a typical antipsychotic or an atypical antipsychotic. Although both typical and atypical antipsychotics are useful for these methods and formulations of the present invention, it is preferred that the first component compound is an atypical antipsychotic.

Typical antipsychotics include, but are not limited to: Chlorpromazine, 2-chloro-10-(3-dimethylaminoprop-yl) phenothiazine, is described in U.S. Pat. No. 2,645,640. Its pharmacology has been reviewed (Crismon, *Psychopharmacol. Bul.* 4, 151 (October 1967): Droperidol, 1-(1-[3-(p-fluorobenzoyl)propyl]-1,2,3,6-tetrahydro-4-pyridyl)-2-benzimidazolinone, is described in U.S. Pat. No. 3,141,823; Haloperidol, 4-[4-(4-chlorophenyl)-4-hydroxy-1-piperidinyl]-1-(4-fluorophenyl)-1-butanone, is described in U.S. Pat. No. 3,438,991. Its therapeutic efficacy in psychosis has been reported (Beresford and Ward, *Drugs*, 33, 31-49 (1987); Thioridazine, 1-hydroxy-10-[2-(1-methyl-2-pyridinyl) ethyl]-2-(methylthio)phenothiazine hydrochloride, was described by Bourquin, et al. (*Helv. Chim. Acta*, 41, 1072 (1958)). Its use as an antipsychotic has been reported (Axelsson, et al., *Curr. Ther. Res.*, 21, 587 (1977)); and Trifluoperazine, 10-[3-(4-methyl-1-piperazinyl)-propyl]-2-trifluoromethylphenthiazine hydrochloride, is described in U.S. Pat. No. 2,921,069.

Atypical antipsychotics include, but are not limited to: Olanzapine, 2-methyl-4-(4-methyl-1-piperazinyl)-10H-thieno[2,3-b][1,5]benzodiazepine, is a known compound and is described in U.S. Pat. No. 5,229,382 as being useful for the treatment of schizophrenia, schizophreniform disorder, acute mania, mild anxiety states, and psychosis; Clozapine, 8-chloro-11-(4-methyl-1-piperazinyl)-5H-dibenzo[b,e][1,4] diazepine, is described in U.S. Pat. No. 3,539,573. Clinical efficacy in the treatment of schizophrenia is described (Hanes, et al., *Psychopharmacol. Bull.*, 24, 62 (1988)); Risperidone, 3-[2-[4-(6-fluoro-1,2-benzisoxazol-3-yl)piperidino]ethyl]-2-methyl-6,7,8,9-tetrahydro-4H-pyrido[1,2-a] pyrimidin-4-one, and its use in the treatment of psychotic diseases are described in U.S. Pat. No. 4,804,663; Sertindole, 1-[2-[4-[5-chloro-1-(4-fluorophenyl)-1H-indol-3-yl]-1-piperidinyl]ethyl]imidazolidin-2-one, is described in U.S. Pat. No. 4,710,500. Its use in the treatment of schizophrenia is described in U.S. Pat. Nos. 5,112,838 and 5,238,945; Quetiapine, 5-[2-(4-dibenzo[b,f][1,4]thiazepin-11-yl-1-piperazinyl)ethoxy]ethanol, and its activity in assays which demonstrate utility in the treatment of schizophrenia are described in U.S. Pat. No. 4,879,288. Quetiapine is typically administered as its (E)-2-butenedioate (2:1) salt; Ziprasidone, 5-[2-[4-(1, 2-benzoisothiazol-3-yl)-1-piperazinyl]ethyl]-6-chloro-1,3-dihydro-2H-indol-2-one, is typically administered as the hydrochloride monohydrate. The compound is described in U.S. Pat. Nos. 4,831,031 and 5,312,925. Its activity in assays which demonstrate utility in the treatment of schizophrenia are described in U.S. Pat. No. 4,831,031; and Aripiprazole (Abilify™), 7-[4-[4-(2,3-dichlorophenyl)-1-piperazinyl]butoxy]-3,4-dihydrocarbostyril (U.S. Pat. Nos. 4,734,416 and 5,006,528) is a new antipsychotic indicated for the treatment of schizophrenia.

It will be understood that while the use of a single antipsychotic as a first component compound is preferred, combinations of two or more antipsychotics may be used as a first component if necessary or desired. Similarly, while the use of a single compound of formula (I) as a second component compound is preferred, combinations of two or more compounds of formula (I) may be used as a second component if necessary or desired.

While all combinations of first and second component compounds are useful and valuable, certain combinations are particularly valued and are preferred, as follows:

olanzapine/compound of formula (I)
clozapine/compound of formula (I)
risperidone/compound of formula (I)
sertindole/compound of formula (I)
quetiapine/compound of formula (I)
ziprasidone/compound of formula (I)
aripiprazole/compound of formula (I)

In general, combinations and methods of treatment using olanzapine as the first component are preferred. It is especially preferred that when the first component is olanzapine, it will be the Form II olanzapine as described in U.S. Pat. No. 5,736,541. It is further preferred that the Form II olanzapine polymorph will be administered as the substantially pure Form II olanzapine polymorph. As used herein "substantially pure" refers to Form II associated with less than about 5% Form I, preferably less than about 2% Form I, and more preferably less than about 1% Form I. Further, "substantially pure" Form II will contain less than about 0.5% related substances, wherein "related substances" refers to undesired chemical impurities or residual solvent or water. In particular, "substantially pure" Form II should contain less than about 0.05% content of acetonitrile, more preferably, less than about 0.005% content of acetonitrile. Additionally, the polymorph of the invention should contain less than 0.5% of associated water. Although Form II olanzapine is preferred it will be understood that as used herein, the term "olanzapine" embraces all solvate and polymorphic forms unless specifically indicated.

Conditions that can be treated by the adjunctive therapy aspect of the present invention include schizophrenia, schizophreniform diseases, bipolar disorder, acute mania, and schizoaffective disorders. The titles given these conditions represent multiple disease states. The following list illustrates a number of these disease states, many of which are classified in the DSM-IV-TR™. The DSM-IV-TR™ code numbers for these disease states are supplied below, when available, for the convenience of the reader.

| | |
|---|---|
| Paranoid Type Schizophrenia | 295.30 |
| Disorganized Type Schizophrenia | 295.10 |
| Catatonic Type Schizophrenia | 295.20 |
| Undifferentiated Type Schizophrenia | 295.90 |
| Residual Type Schizophrenia | 295.60 |
| Schizophreniform Disorder | 295.40 |
| Schizoaffective Disorder | 295.70 |

The present invention also encompasses the use of one or more compounds of formula (I) that selectively inhibit the reuptake of norepinephrine over serotonin and dopamine in combination with one or more conventional Alzheimer's agents for the prevention or treatment of cognitive dysfunction in patients suffering from Alzheimer's disease. The invention also provides a pharmaceutical composition which comprises a first component that is a conventional Alzheimer's agent and a second component that is a compound of formula (I) that selectively inhibits the reuptake of norepinephrine over serotonin and dopamine. Conventional Alzheimer's agents include inhibitors of acetylcholine degradation (i.e., cholinesterase or acetylcholinesterase inhibitors) within synapses, e.g., donepezil (Aricept®), rivastigmine (Exelon®), galantamine (Reminyl®), and tacrine (Cognex®); the selective monoamine oxidase inhibitor selegiline (Eldepryl®); and memantine (Namenda™), a newly FDA-approved NMDA receptor antagonist for the treatment of moderate to severe Alzheimer's disease. Modafinil (Provigil®) is also used in the treatment of Alzheimer's disease.

The present invention also encompasses the use of one or more compounds of formula (I) that selectively inhibit the reuptake of norepinephrine over serotonin and dopamine in combination with one or more conventional Parkinson's agents for the treatment of cognitive dysfunction in Parkinson's disease. The invention also provides a pharmaceutical composition which comprises a first component that is a conventional Parkinson's agent and a second component that is a compound of formula (I) that selectively inhibits the reuptake of norepinephrine over serotonin and dopamine. Conventional Parkinson's agents include levodopa; levodopa/carbidopa (Sinemet®); Stalevo (carbidopa/levodopa/entacapone); dopamine agonists, e.g., bromocriptine; pergolide; Mirapex® (pramipexole), Permax® (pergolide), and Requip® (ropinirole); COMT inhibitors, e.g., tolcapone, and entacapone; Selegiline (Deprenyl®; Eldepryl®); propranolol; primidone; anticholinergics, e.g., Cogentin®, Artane®, Akineton®, Disipal®, and Kemadrin®; and amantadine.

In each of the combination treatments mentioned above, said first and second components may be administered simultaneously, separately or sequentially. Similarly, said compositions encompass combined preparations for simultaneous, separate or sequential use.

Another preferred group of compounds of the present invention selectively inhibit the reuptake of norepinephrine, serotonin and dopamine. Compounds of the present invention with this pharmacological profile are particularly useful for the treatment of a variety of conditions such as depression, obesity, compulsive disorders (including bulimia, obsessive compulsive disorder, drug addiction including cocaine abuse and alcohol addiction), hypertension, senile dementia, Alzheimer's, memory loss, attention-deficit hyperactivity disorder (ADHD), sexual dysfunction, Parkinsonism, anxiety, chronic fatigue syndrome, panic disorders, cognitive disorders, schizophrenia, gastrointestinal disorders, headache, cardiovascular disorders, epilepsy, smoking cessation, pain including chronic pain, urinary incontinence, emesis and sleep disorders. They are most particularly useful for the treatment of depression, chronic pain, smoking cessation and obesity.

Accordingly, the present invention provides a compound of Formula (I) or a pharmaceutically acceptable salt thereof for use in therapy. In particular, the present invention provides a compound of Formula (I) or a pharmaceutically acceptable salt thereof for use as an inhibitor of the uptake of one or more of the monoamine neurotransmitters serotonin, dopamine and norepinephrine.

In another embodiment, the present invention provides a method for inhibiting the uptake of one or more monoamines selected from serotonin, dopamine and norepinephrine in a mammal, comprising administering to a mammal in need of such inhibition an effective amount of a compound of Formula (I) or a pharmaceutically acceptable salt thereof. In particular, the present invention provides a method for treating a disorder which is caused by or linked to decreased neurotransmission of one or more monoamines selected from serotonin, dopamine and norepinephrine in a mammal, comprising administering to a mammal in need of such treatment an effective amount of a compound of Formula (I) or a pharmaceutically acceptable salt thereof. Such disorders include, for example, disorders of the central and/or peripheral nervous system. Examples of disorders of the central and/or peripheral nervous system are specifically identified above.

It is recognized that the terms "treatment" and "treating" are intended to include improvement of the disorders described herein. Thus, the terms "treatment" and "treating" are intended to refer to all processes wherein there may be a slowing, interrupting, arresting, controlling, or stopping of the progression of the disorders described herein, but does not necessarily indicate a total elimination of all symptoms, and is intended to include prophylactic treatment of such disorders.

In another alternative embodiment, the present invention provides for the use of a compound of Formula (I) or a pharmaceutically acceptable salt thereof for the manufacture of a medicament for inhibiting the uptake of one or more monoamines selected from serotonin, dopamine and norepinephrine. In particular, the present invention provides for the use of a compound of Formula (I) or a pharmaceutically acceptable salt thereof for the manufacture of a medicament for the treatment of a disorder which is caused by or linked to decreased neurotransmission of one or more monoamines selected from serotonin, dopamine and norepinephrine. Such disorders include, for example, disorders of the central and/or peripheral nervous system. Examples of disorders of the central and/or peripheral nervous system are specifically identified above.

The compounds may be administered by various routes and are usually employed in the form of a pharmaceutical composition.

Accordingly, in a further embodiment, the present invention provides a pharmaceutical composition comprising a compound of Formula (I) or a pharmaceutically acceptable salt thereof together with a pharmaceutically acceptable diluent or carrier.

Such compositions may be prepared by methods well known in the pharmaceutical art and normally comprise at least one active compound in association with a pharmaceutically acceptable diluent or carrier. In making the compositions of the present invention, the active ingredient will usually be mixed with a carrier or diluted by a carrier, and/or enclosed within a carrier which may, for example, be in the form of a capsule, sachet, paper or other container.

The compositions indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds. Compositions of the invention may be formulated so as to provide, quick, sustained or delayed release of the active ingredient after administration to the patient by employing procedures well known in the art.

The compositions are preferably formulated in a unit dosage form, each dosage containing from about 5 to about 500 mg of the active ingredient.

In the context of the present specification, the term "unit dosage form" refers to physically discrete units suitable as unitary doses for human subjects and other mammals, each unit containing a predetermined quantity of one or more compounds of Formula (I) or pharmaceutically acceptable salts thereof, calculated to produce the desired therapeutic effect, together with a pharmaceutically acceptable diluent or carrier.

Compounds of formula (I) may be prepared by conventional organic chemistry techniques and also by solid phase synthesis.

Compounds of formula (I') can be prepared by the general methods illustrated below. It will be appreciated that the same methods can be used for compounds of formula (I″) with the only difference that the nitrogen atom of the quinuclidines does not need to be protected as it is already a tertiary amine as it is explained in more detail below with reference to Scheme 1′.

Compounds of formula (I′) can be prepared via the 3-aminopiperidine intermediate of formula (IV) as illustrated in Scheme 1 below:

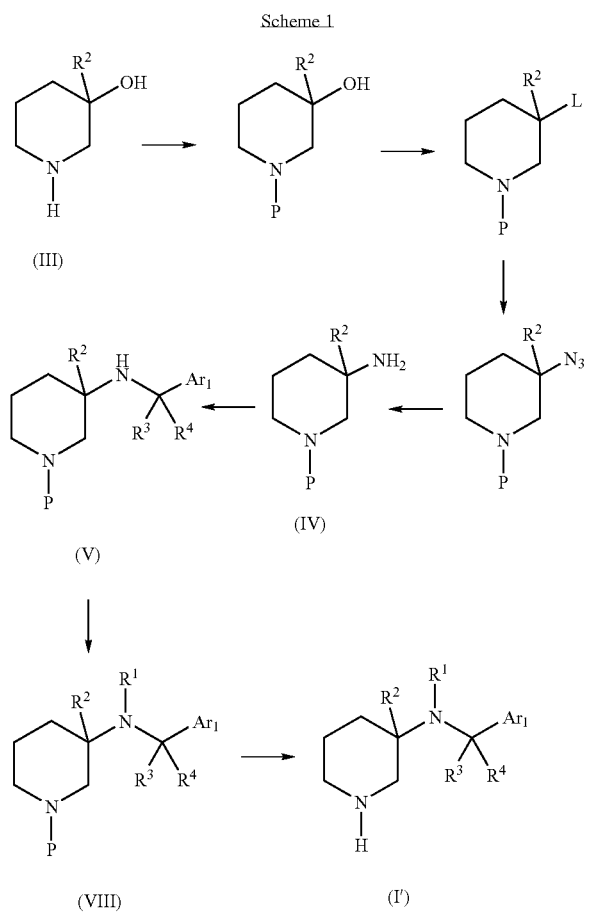

(V)    (IV)    (III)

(VIII)    (I′)

Commercially available 3-hydroxypiperidine of formula (III) wherein $R^2$ is hydrogen, can be protected using a suitable nitrogen-protecting group such as those described in T. W. Greene, "Protective Groups in Organic Synthesis", John Wiley and Sons, New York, N.Y., 1991, hereafter referred to as "Greene". For example 3—R-hydroxypiperidine (III) can be protected with a tert-butoxycarbonyl group, (boc). The protection reaction can be carried out for example using Boc anhydride in a suitable solvent such as for example tetrahydrofuran (THF) or dichloromethane (DCM) in the presence of a base such as triethylamine (TEA) or 4-(dimethylamino) pyridine (DMAP). It will be appreciated that for compounds of formula (I) wherein $R^2$ is $C_1$-$C_2$alkyl, the 3-hydroxypiperidine of formula (III) can be prepared from the readily available 3-pyrrolidinone via addition of the appropriate $C_1$-$C_2$alkyl organometallic.

The hydroxy group of the N-protected-3-hydroxypiperidine can be converted into a suitable leaving group (L) such as for example chloride, bromide, iodide or mesylate. For example the N-protected-hydroxypiperidine can be converted to the mesylate in the presence of mesyl chloride and a suitable base such as triethylamine in a solvent such as DCM.

Said mesylate is subsequently displaced with the corresponding azide in a suitable solvent such as dimethylformamide (DMF) or dimethylsulphoxide (DMSO). This azide intermediate can be converted to the corresponding N-protected-aminopiperidine of formula (IV) via hydrogenation in the presence of a suitable catalyst such as Palladium on charcoal and in a suitable solvent such as methanol or ethanol.

For compounds of formula (I) wherein $R^4$ is H, intermediate (IV) can be alkylated via reductive alkylation with a ketone of formula $R^3$—CO—$Ar_1$ wherein $R^3$ and $Ar_1$ have the values for formula (I) above. The reductive alkylation can be carried out for example as a hydrogenation reaction in the presence of a suitable catalyst such as Palladium on charcoal and a suitable solvent such as for example ethanol. Alternatively, said reductive alkylation can be carried out in the presence of a suitable borane such as sodium triacetoxyborohydride, $NaBH(OAc)_3$ and optionally in the presence of a suitable acid such as acetic acid, in a suitable solvent such as for example dichoroethane (DCE).

Alternatively, intermediate of formula (V) wherein $R^4$ is H can be prepared as shown in Scheme 2 below by reductive alkylation of readily available 3-aminopiperidine of formula (VI) wherein $R^2$ has the values defined for formula (I) above, followed by the protection of the nitrogen in the piperidine ring using a suitable protecting group such as those defined in Greene.

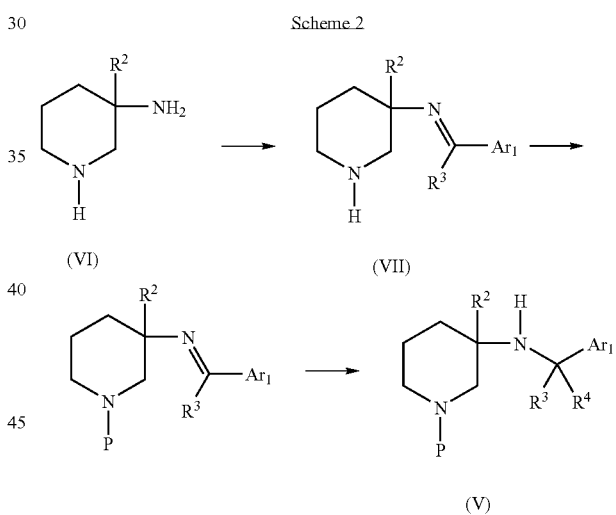

(VI)    (VII)

(V)

For example the reductive alkylation can be carried out in the presence of a ketone of formula $Ar_1$—CO—$R^3$ wherein $Ar_1$ and $R^3$ have the values defined for formula (I) above. Initial condensation of the amino piperidine with the ketone is undertaken in the presence of a suitable acid such as p-toluenesulphonic acid, in a suitable solvent such as toluene. The resultant imino piperidine intermediate can then be protected with for example a boc group. The reaction can be carried out in the presence of boc anhydride and a suitable base such as DMAP, in a suitable solvent such as DCM. Said imine is reduced via hydrogenation in the presence of a suitable catalyst such as palladium on charcoal, in a suitable solvent such as ethanol to give the corresponding amine of formula (V).

Intermediate of formula (V) can be converted to compounds of formula (VIII) via reductive alkylation with an aldehyde of formula $R^9$—CHO, wherein $R^9$ is chosen such that $R^9$—$CH_2$=$R^1$ and $R^1$ has the values defined for formula (I) above. The reductive alkylation can be carried out using standard methods, for instance as those mentioned above with the ketone $Ar_1$—CO—$R^3$.

Scheme 3

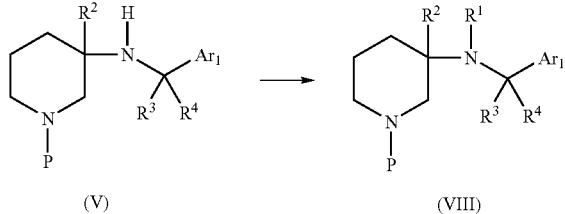

(V)　　　　　　　　　　　(VIII)

For example a compound of formula (V) can be alkylated with $R^9$—CHO in the presence of a suitable borane, such as $NaBH(OAc)_3$, optionally in the presence of an acid such as acetic acid, in the presence of a suitable solvent such as dichloroethane (DCE).

For compounds of formula (I) wherein $R^3$ and $R^4$ are hydrogen the alkylation of intermediate (V) can be carried out with a compound of formula $Ar_1CH_2L_1$ wherein $L_1$ is a suitable leaving group such as chloro, bromo, iodo or mesylate, in the presence of a suitable base such as potassium carbonate and a suitable solvent such as acetonitrile, to give the corresponding intermediate of formula $(VIII)_a$. It will be appreciated that the same reaction can be carried out using $Ar_1$—$CR^3R^4$-L, wherein $R^3$ and $R^4$ are $C_1$-$C_2$alkyl.

Scheme 4

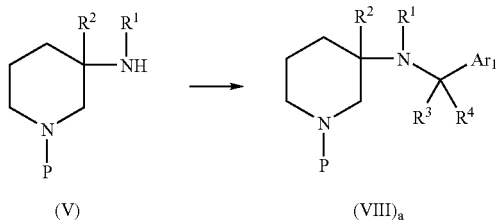

(V)　　　　　　　　　　　$(VIII)_a$

Compounds of formula (I) wherein $R^1$ is —$CH_2$—COO—($C_1$-$C_2$alkyl) can be prepared by reacting intermediate (V) with a compound of formula $L_2$-$CH_2$—COO—($C_1$-$C_2$alkyl) wherein $L_2$ is a suitable leaving group such as for example bromo, chloro or iodo. Said reaction can be carried out in the presence of a suitable base such as sodium hydride, in a suitable solvent such as dimethylformamide.

Scheme 5

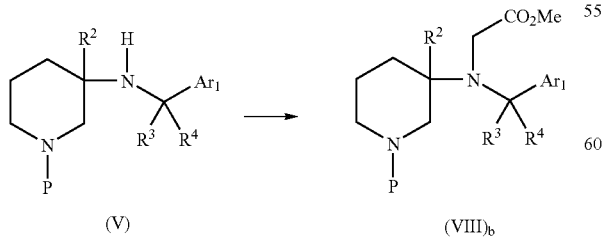

(V)　　　　　　　　　　　$(VIII)_b$

Compounds of formula (I) wherein $R^1$ is $(CH_2)_m$—$CF_3$ can be prepared by reacting intermediate (V) with a compound of formula HOOC—$(CH_2)_{(m-1)}$—$CF_3$. The acid may be activated as its anhydride or acyl chloride, and is reacted in the presence of a suitable base such as triethylamine and a catalytic amount of DMAP, in a suitable solvent such as DCM. The resulting amide can be reduced to the amine of formula $(VIII)_c$ in the presence of a suitable borane. For example, for compounds wherein m is 1, the reduction can be carried out in the presence of $BH_3$-$Me_2S$ borane-dimethyl sulphide complex, in a suitable solvent such as THF.

Scheme 6

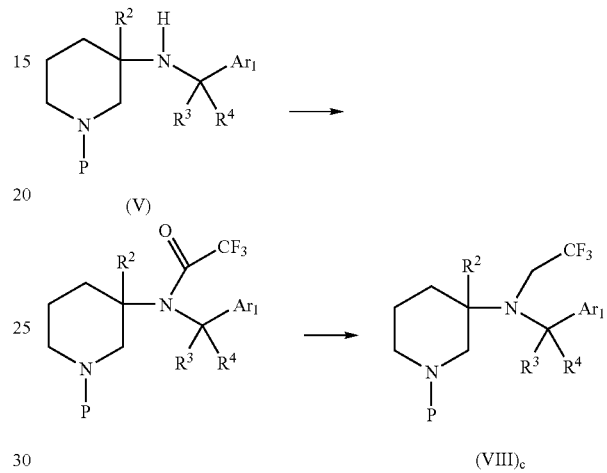

$(VIII)_c$

Compounds of formula (I) wherein $R^1$ is —($C_1$-$C_6$alkylene)-OH can be prepared by reacting intermediate (V) with an epoxide. For example for compounds wherein $R^1$ is —$CH_2$—$C(CH_3)_2$—OH, the intermediate of formula (V) is reacted with 2,2-dimethyloxirane, in a suitable solvent such as aqueous ethanol.

Scheme 7

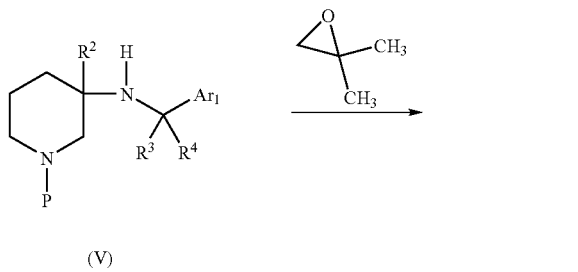

$(VIII)_d$

Alternatively compounds of formula (I) wherein $R^1$ is —$C_1$-$C_6$alkylene)-OH can be prepared by reacting intermediate (V) with an ω-haloalkanoate, such as methylbromoacetate, in the presence of a base such as a sodium hydrogen carbonate in a solvent such as acetonitrile. The intermediate ester is then reacted with 2 equivalents of methyl magnesium bromide in THF to yield the tertiary alcohol (VIII)$_d$:

Scheme 8

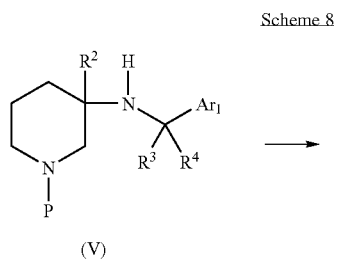

(V)

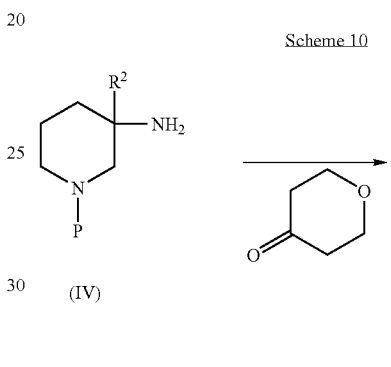

(VIII)$_d$

It will be appreciated that the Scheme 8 above applies to alkylene chains longer than —$CH_2$—.

Compounds of formula (I) wherein $R^1$ is —$C_2$-$C_6$alkenyl, —($CH_2$), —S—($C_1$-$C_3$alkyl), —($C_1$-$C_5$alkylene)-O—($C_1$-$C_3$alkyl), —($C_1$-$C_5$alkylene)-O—($C_3$-$C_6$cycloalkyl), —($C_1$-$C_5$alkylene)-$SO_2$—($C_1$-$C_3$alkyl), —($C_1$-$C_5$alkylene)-$OCF_3$, or —($C_1$-$C_5$alkylene)-CN, can be prepared via alkylation of intermediate (V) with a compound of formula $L_2$-$C_2$-$C_6$alkenyl, $L_2$-($CH_2$)$_n$—S—($C_1$-$C_3$alkyl), $L_2$-($C_1$-$C_5$alkylene)-O—($C_1$-$C_3$alkyl), $L_2$-($C_1$-$C_5$alkylene)-O—($C_3$-$C_6$cycloalkyl), $L_2$-($C_1$-$C_5$alkylene)-$SO_2$—($C_1$-$C_3$alkyl), $L_2$-($C_1$-$C_5$alkylene)-$OCF_3$, or $L_2$-($C_1$-$C_5$alkylene)-CN respectively, wherein $L_2$ is a suitable leaving group such as chloro, bromo, iodo or mesylate, in the presence of a suitable base such as potassium carbonate and a suitable solvent such as acetonitrile, to give the corresponding intermediate of formula (VIII)$_e$.

Scheme 9

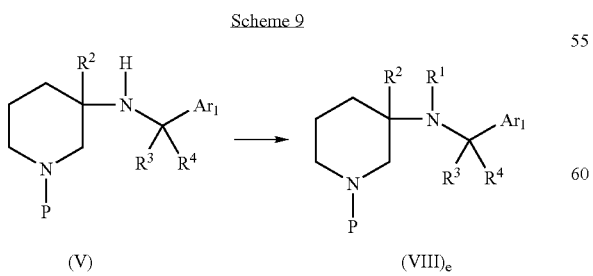

(V)                                    (VIII)$_e$

Compounds of formula (I) wherein $R^1$ is a group of formula (i) can be prepared using the synthesis illustrated in Scheme 10 for compounds wherein $R^1$ is 4-tetrahydropyranyl. The compound of formula (IV) can be alkylated via reductive alkylation using standard methods, as those mentioned above with the ketone $Ar_1$—CO—$R^3$. For example a compound of formula (IV) can be alkylated with 4-tetrahydropyranone in the presence of a suitable borane, such as sodium borohydride or NaBH(OAc)$_3$, optionally in the presence of an acid such as acetic acid, in the presence of a suitable solvent such as dichloroethane (DCE). Then, the secondary amine can be alkylated with a compound of formula $Ar_1CH_2L_1$ wherein $L_1$ is a suitable leaving group such as chloro, bromo, iodo or mesylate, in the presence of a suitable base such as potassium carbonate and a suitable solvent such as acetonitrile; to give the corresponding intermediate of formula (VIII)$_f$. It will be appreciated that as mentioned above the same reaction can be carried out using $Ar_1$—$CR^3R^4$-$L_1$, wherein $R^3$ and $R^4$ are $C_1$-$C_2$alkyl.

Scheme 10

(IV)

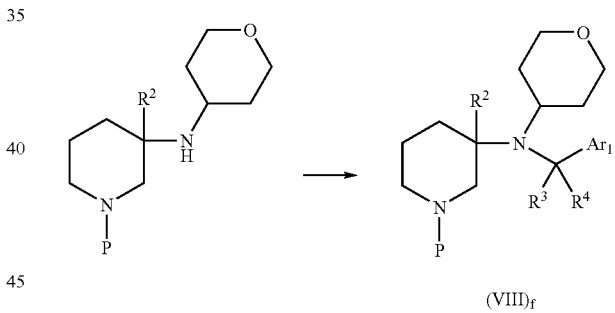

(VIII)$_f$

It will be appreciated that for compounds of formula (I) wherein $R^1$ is a group of formula (i) and r is 1 then the reductive amination can be carried out using the same reaction conditions but using the corresponding homologous aldehyde of formula

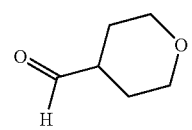

instead of the corresponding 4-tetrahydropyranone. Alternatively, compounds of formula (I) wherein $R^1$ is a group of formula (i) and r is 1 can be prepared via formation of an amide, followed by reduction of this amide bond to the corresponding amine as shown in Scheme 11 below:

Scheme 11

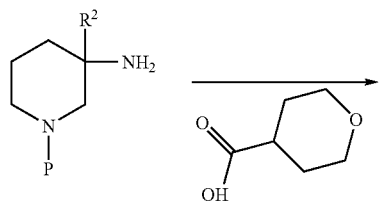

(IV)

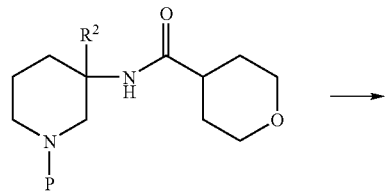

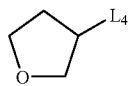

(VIII)$_g$

The coupling reaction can be carried out using standard methods known in the art. The reduction of the amide bond can also be carried out by general methods known in the art for example using the same reduction conditions as those used in Scheme 6, such as in the presence of $BH_3$-$Me_2S$ (borane-dimethyl sulphide complex), in a suitable solvent such as THF.

Alternatively, compounds of formula (I) wherein $R^1$ is a group of formula (i) wherein r is 0 can be prepared by a process illustrated in Scheme 12 for compounds wherein -Z is hydrogen, s is 1, t is 2, each $R^5$, $R^6$, $R^7$ and $R^8$ are hydrogen and —X— is —O—, (i.e. $R^1$ is tetrahydrofuran-3-yl). The compound of formula (IV) can be alkylated with a compound of formula:

wherein $L_4$ is a suitable leaving group such as chloro, bromo, iodo, mesylate or tosylate, in the presence of a suitable base such as potassium carbonate and a suitable solvent such as acetonitrile, to give the corresponding secondary amine which can be subsequently alkylated with a compound of formula $Ar_1CH_2L_1$ wherein $L_1$ is a suitable leaving group such as chloro, bromo, iodo or mesylate, in the presence of a suitable base such as potassium carbonate and a suitable solvent such as acetonitrile, to give the corresponding intermediate of formula (VIII)$_f$. It will be appreciated that as mentioned above the same reaction can be carried out using $Ar_1$—$CR^3R^4$-L, wherein $R^3$ and $R^4$ are $C_1$-$C_2$alkyl.

Scheme 12

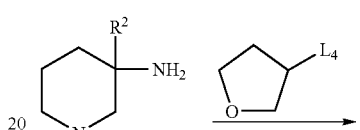

(V)

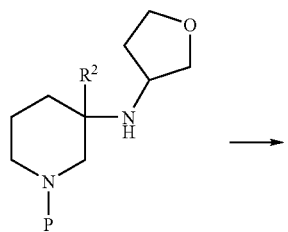

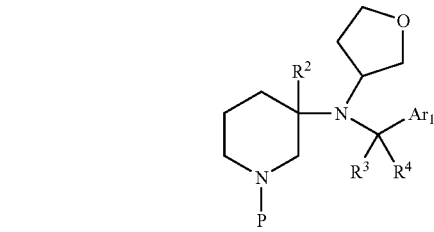

(VIII)$_h$

The tetrahydrofuranyl intermediates can be prepared from the corresponding 3-hydroxytetrahydrofuran, wherein the hydroxy group is converted into the leaving group using standard methods.

Compounds of formula (I) wherein $R^1$ is a group of formula (i) and —X— is —$SO_2$— can be prepared from the corresponding intermediates (VIII)$_f$, wherein the thioether is oxidized to the corresponding sulphoxide as shown in Scheme 13 below:

Scheme 13

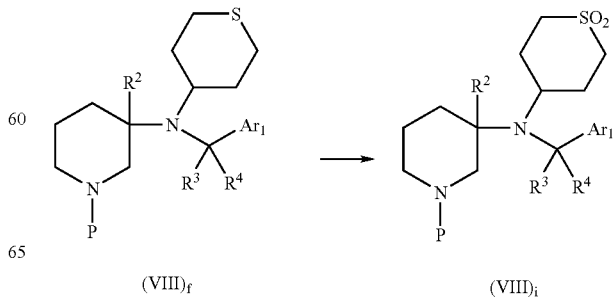

(VIII)$_f$       (VIII)$_i$

Compounds of formula (I) wherein $R^1$ is a group of formula (ii) can be prepared using the synthesis illustrated in Scheme 14 for compounds wherein $R^1$ is oxabicyclo[3,2,1]octan-3-yl. The compound of formula (IV) can be alkylated via reductive alkylation using standard methods, as those mentioned above with the ketone $Ar_1$—CO—$R^3$. For example compound of formula (IV) can be alkylated with oxabicyclo[3,2,1]octan-3-one in the presence of a suitable borane, such as sodium borohydride or $NaBH(OAc)_3$, optionally in the presence of an acid such as acetic acid, in the presence of a suitable solvent such as dichloroethane (DCE). Then, the secondary amine can be alkylated with a compound of formula $Ar_1CH_2L_1$ wherein $L_1$ is a suitable leaving group such as chloro, bromo, iodo or mesylate, in the presence of a suitable base such as potassium carbonate and a suitable solvent such as acetonitrile, to give the corresponding intermediate of formula (VIII)$_j$. It will be appreciated that as mentioned above the same reaction can be carried out using $Ar_1$—$CR^3R^4$-$L_1$ wherein $R^3$ and $R^4$ are $C_1$-$C_2$alkyl.

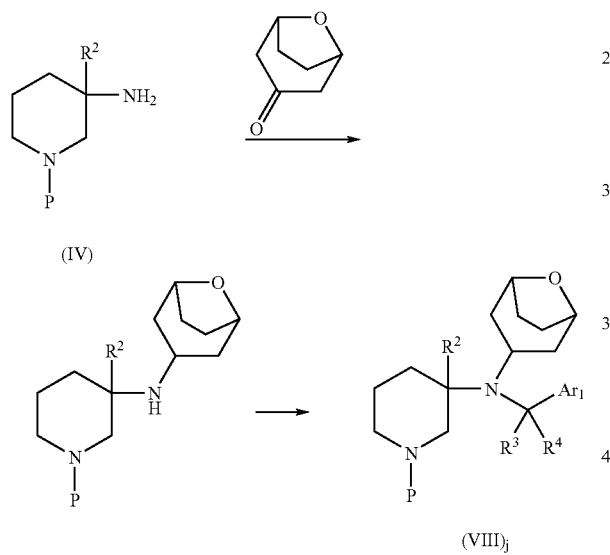

(VIII)$_j$

The oxabicyclo[3,2,1]octan-3-one intermediate is prepared according to the method described in A E Hill, G Greenwood and H M R Hoffmann JACS 1973, 95, 1338. It will be appreciated that for compounds of formula (I) wherein $R^1$ is a group of formula (i) and r is 1 then the reductive amination can be carried out using the same reaction conditions but using the corresponding homologous aldehyde of formula

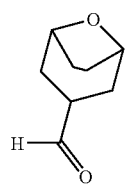

instead of the corresponding oxabicyclo[3,2,1]octan-3-one.

Compounds of formula (I) wherein $Ar_1$ is a substituted or unsubstituted pyridyl group can be prepared by a process illustrated in Scheme 15 for compounds wherein $R^3$ and $R^4$ are hydrogen and $Ar_1$ is 3-phenylpyrid-2-yl.

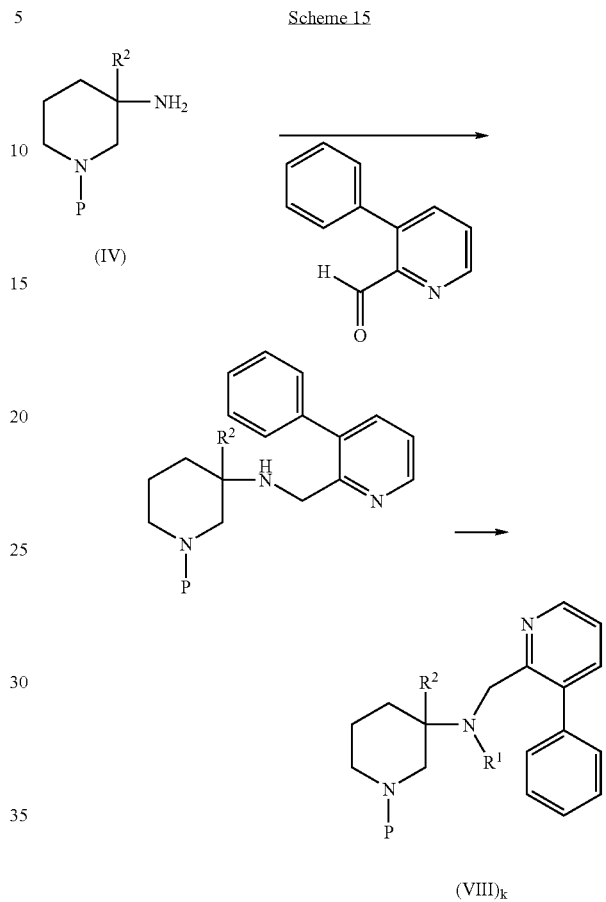

(VIII)$_k$

The compound of formula (IV) can be alkylated via reductive alkylation using standard methods, as those mentioned above with the ketone $Ar_1$—CO—$R^3$. For example compound of formula (IV) can be alkylated with an aldehyde of formula:

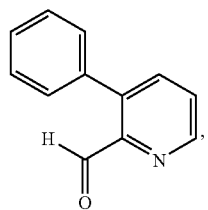

in the presence of a suitable borane, such as sodium borohydride or $NaBH(OAc)_3$, optionally in the presence of an acid such as acetic acid, in the presence of a suitable solvent such as dichloroethane (DCE). Then, the secondary amine can be alkylated using the general methods described above for the incorporation of $R^1$. The intermediate aldehyde can be prepared via reduction of readily available methyl 3-phenyl picolinate to the corresponding alcohol and subsequent oxidation to the aldehyde as shown in Scheme 16 below.

Scheme 16

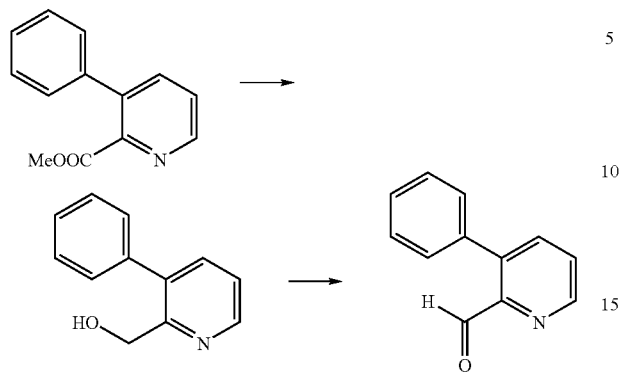

The reduction step can be carried out in the presence of a suitable reducing agent such as lithium borohydride in a suitable solvent such as tetrahydrofuran. The oxidation to the aldehyde can be carried out under Swern conditions such as oxalyl chloride and DMSO in DCM.

Compounds of formula (I) wherein $Ar_1$ is a substituted or unsubstituted phenyl group can be prepared by a process illustrated in Scheme 17 for compounds wherein $R^3$ and $R^4$ are hydrogen and $Ar_1$ is 2-(3-pyridyl)phenyl.

Scheme 17

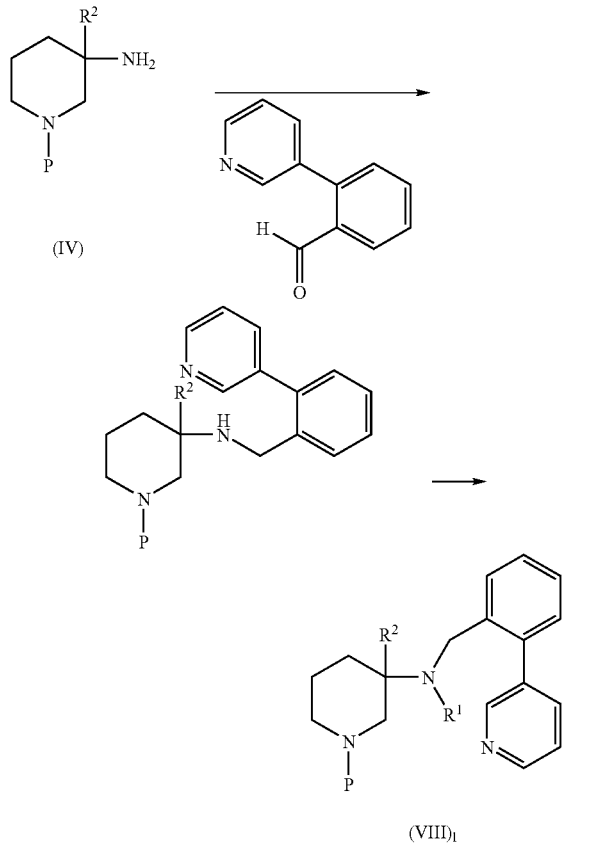

The compound of formula (IV) can be alkylated via reductive alkylation using standard methods, as those mentioned above with the ketone $Ar_1$—CO—$R^3$. For example compound of formula (IV) can be alkylated with an aldehyde of formula:

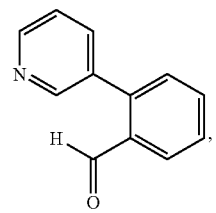

in the presence of a suitable borane, such as sodium borohydride or $NaBH(OAc)_3$, optionally in the presence of an acid such as acetic acid, in the presence of a suitable solvent such as dichloroethane (DCE). Then, the secondary amine can be alkylated using the general methods described above for the incorporation of $R^1$. The intermediate aldehyde can be prepared from the commercially available 2-formyl phenyl boronic acid via palladium coupling in the presence of 3-bromopyridine, a suitable palladium catalyst such as $Pd(PPh_3)_4$ and a suitable base such as potassium carbonate in a suitable solvent such as acetonitrile, as shown in Scheme 18 below.

Scheme 18

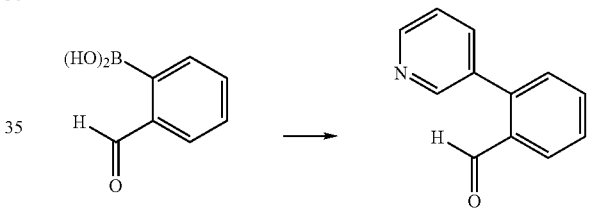

Compounds of formula (I) wherein $Ar_1$ is a phenyl group substituted with a 1-pyrazole group can be prepared by a process illustrated in Scheme 19.

Scheme 19

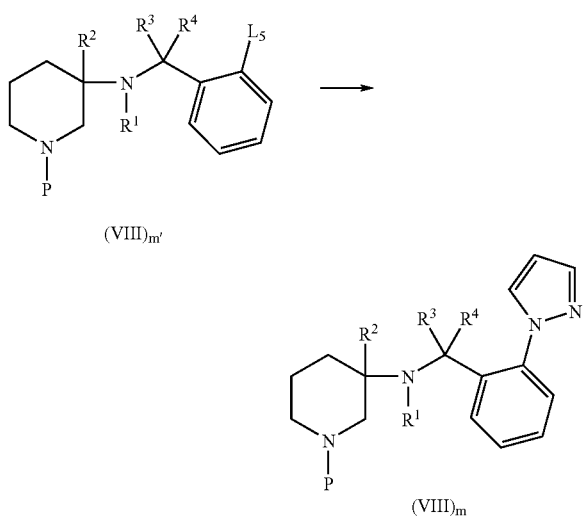

The pyrazole group can be incorporated by reacting a compound of formula (VIII)$_{m'}$, wherein $L_5$ is a suitable leaving group such as bromo, chloro or iodo, with pyrazole in the presence of a suitable base such as potassium carbonate and a catalytic amount of copper iodide in a suitable solvent such as for example DMF. The compound of formula (VIII)$_{m'}$ can be prepared by any of the methods mentioned above for compounds wherein $Ar_1$ is a phenyl group substituted with a halogen atom such as chloro, bromo or iodo.

It will be appreciated that any of the intermediates (VIII), (VIII)$_{a-m}$ are then deprotected using suitable deprotecting conditions such as those discussed in Greene, to give the corresponding compounds of formula (I). For example if the protecting group is a boc group, the deprotection reaction can be carried out in trifluoroacetic acid in a suitable solvent such as DCM. Alternatively the reaction can be carried out in ethanolic hydrochloric acid.

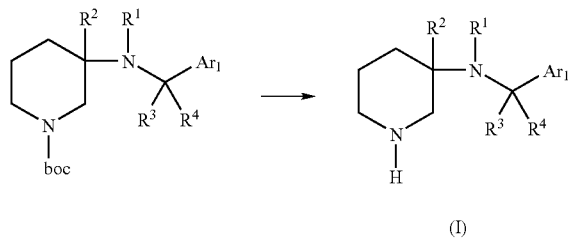

Scheme 20

(I)

Compounds of formula (I) wherein $R^3$ and $R^4$ are both hydrogen may also be prepared by solid phase synthesis by the route shown below.

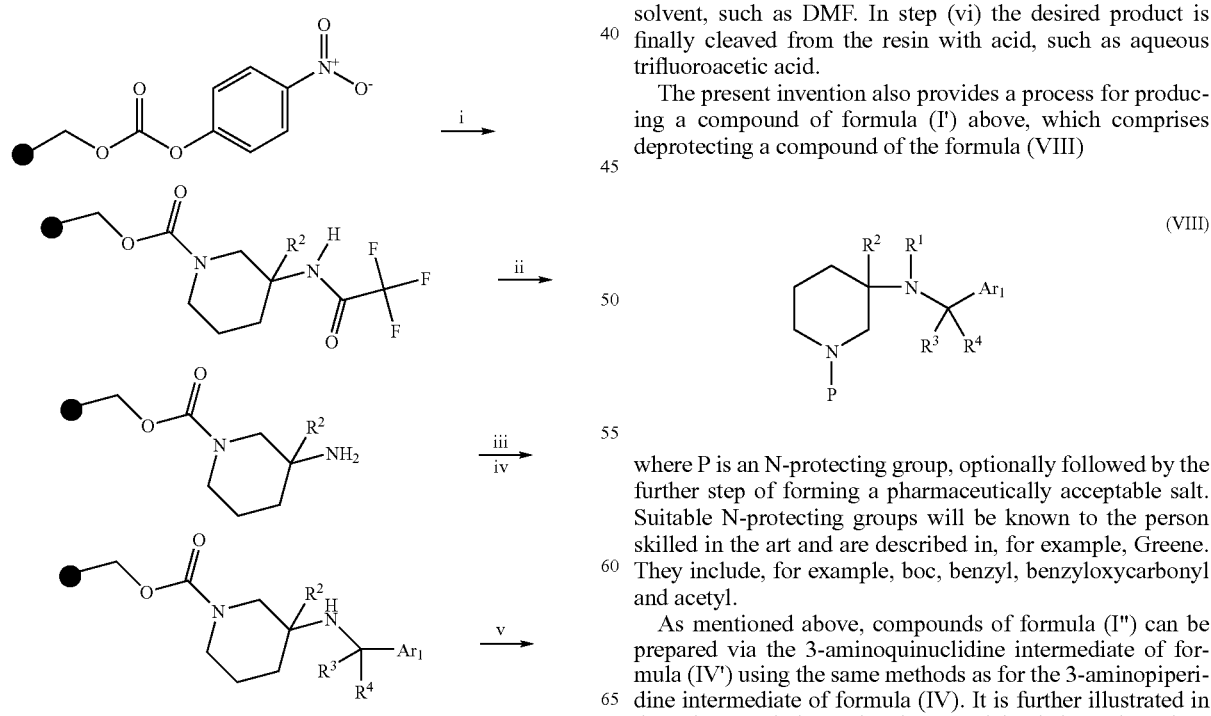

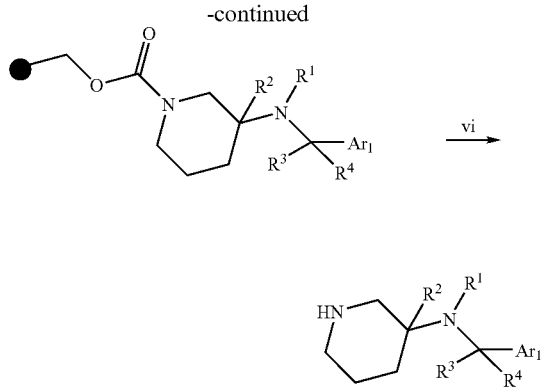

The sequence is preferably performed on a polystyrene resin. The process may be run in a combinatorial fashion such that all possible compounds from sets of precursors $Ar_1CHO$ and $R^9CHO$ may be prepared, wherein $R^9$ is chosen such that $R^9$—$CH_2$=$R^1$, and $R^1$ and $Ar_1$ have the values defined above for formula (I). The sequence is performed without characterisation of the resin-bound intermediates. In step (i) 3-trifluoroacetamidopiperidine is bound to a solid support by reaction with 4-nitrophenyl carbonate activated polystyrene resin in the presence of a base, such as N,N-diisopropylethylamine, in a solvent such as DMF. In step (ii), the trifluoroacetamido protecting group is cleaved by hydrolysis with a base such as aqueous lithium hydroxide. In step (iii) the primary amine is then condensed with a substituted benzaldehyde in the presence of a dehydrating agent, such as trimethylorthoformate, to form the intermediate imine. In step (iv) the imine is reduced with a borane reducing agent, such as sodium cyanoborohydride, in a solvent such as DMF, containing acetic acid. In step (v) the resultant secondary amine is then reductively alkylated with an aldehyde in the presence of a reducing agent such as sodium triacetoxyborohydride in a solvent, such as DMF. In step (vi) the desired product is finally cleaved from the resin with acid, such as aqueous trifluoroacetic acid.

The present invention also provides a process for producing a compound of formula (I') above, which comprises deprotecting a compound of the formula (VIII)

(VIII)

where P is an N-protecting group, optionally followed by the further step of forming a pharmaceutically acceptable salt. Suitable N-protecting groups will be known to the person skilled in the art and are described in, for example, Greene. They include, for example, boc, benzyl, benzyloxycarbonyl and acetyl.

As mentioned above, compounds of formula (I'') can be prepared via the 3-aminoquinuclidine intermediate of formula (IV') using the same methods as for the 3-aminopiperidine intermediate of formula (IV). It is further illustrated in the Scheme 1' below, wherein as explained above the quinuclidine does not need to be protected:

Scheme 1'

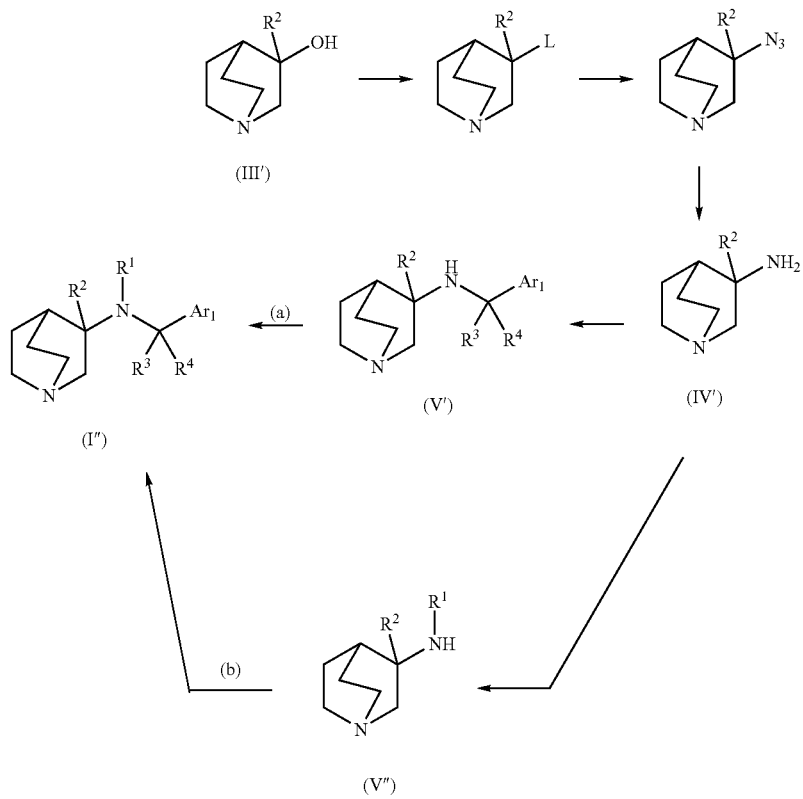

Intermediate of formula (IV') wherein $R^2$ is hydrogen, 3-aminoquinuclidine, is commercially available. For compounds of formula (I") wherein $R^2$ is $C_1$-$C_2$alkyl, the 3-hydroxyquinuclidine of formula (III') can be prepared from the commercially available 3-quinuclidinone via addition of the appropriate $C_1$-$C_2$alkyl organometallic. Then, the hydroxy group can be converted into a suitable leaving group (L) such as for example chloride, bromide, iodide or mesylate as illustrated in Scheme 1 above, via the methods mentioned above for the piperidine derivatives.

The present invention also provides a process for producing a compound of formula (I") above, which comprises either (a) reacting a compound of the formula (V')

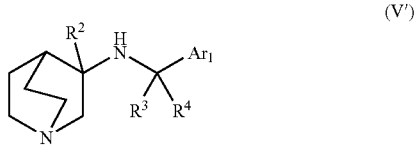

(V')

with an aldehyde of formula $R^9$—CHO, wherein $R^9$ is chosen such that $R^9$—$CH_2$=$R^1$ and $R^1$ has, toe values defined for formula (I) above, in the presence of a suitable reducing agent, or (b) reacting a compound of formula

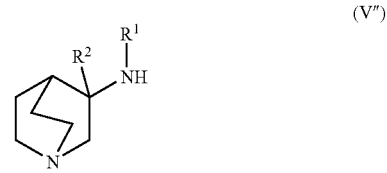

(V")

with (i) a compound of formula $Ar_1$—$CR^3R^4$-$L_1$, wherein $Ar_1$, $R^3$ and $R^4$ have the values defined for formula (I) above and $L_1$ is a suitable leaving group such as chloro, bromo, iodo or mesylate, in the presence of a suitable base, or
(ii) a compound of formula $Ar_1$—CO—$R^3$, wherein $Ar_1$, and $R^3$ have the values defined for formula (I) above, in the presence of a suitable reducing agent.

The following synthetic methods illustrate further processes for the preparation of a compound of formula (I") above. It will be understood that the reagents used in each synthetic method are those mentioned above for the schemes with the same number. It will be appreciated that the last step of each synthesis also represent further aspects of the present invention. Compounds of formula (I") wherein:

(i) $R^1$ is —($C_1$-$C_5$alkylene)-$CO_2$—($C_1$-$C_2$alkyl) can be prepared by reacting intermediate (V) with a compound of formula $L_2$-($C_1$-$C_2$alkylene)-$CO_2$—($C_1$-$C_2$alkyl)

wherein $L_2$ is a suitable leaving group such as for example bromo, chloro or iodo:

Scheme 5'

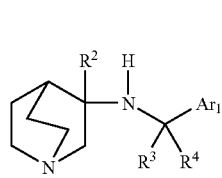

(V')

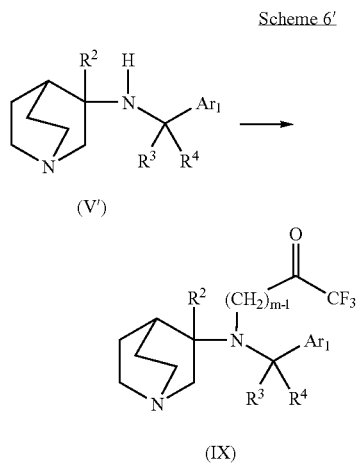

(VIII')$_b$ (ii) $R^1$ is —$(CH_2)_m$—$CF_3$ can be prepared by reducing an amide intermediate (IX) with a suitable reducing agent;

Scheme 6'

(V')

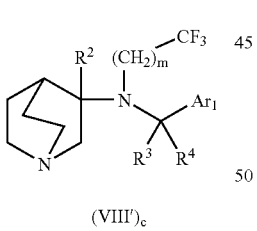

(IX)

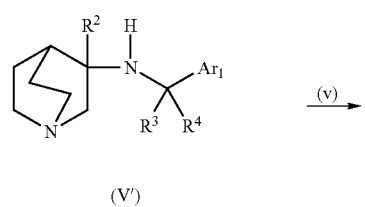

(VIII')$_c$ (iii) $R^1$ is —$(C_1$-$C_6$alkylene)-OH can be prepared by reacting intermediate (V') with a suitable epoxide;

Scheme 7'

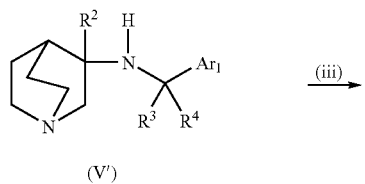

(V')

-continued

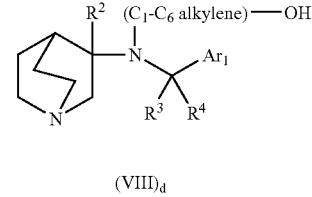

(VIII')$_d$ (iv) $R^1$ is —$C_1$-$C_6$alkylene)-OH can be prepared by reacting intermediate (V') with suitable organometalic compounds;

Scheme 8'

(V')

(VIII')$_d$ (v) $R^1$ is —$C_2$-$C_6$alkenyl, —$(CH_2)_n$—S—$(C_1$-$C_3$alkyl), —$(C_1$-$C_5$alkylene)-O—$(C_1$-$C_3$alkyl), —$(C_1$-$C_5$alkylene)-O—$(C_3$-$C_6$cycloalkyl), —$(C_1$-$C_5$alkylene)-SO$_2$—$(C_1$-$C_3$ alkyl), —$(C_1$-$C_5$alkylene)-OCF$_3$, or —$(C_1$-$C_5$alkylene)-CN, can be prepared via alkylation of intermediate (V') with a compound of formula $L_2$-$C_2$-$C_6$alkenyl, $L_2$-$(CH_2)_n$—S—$(C_1$-$C_3$alkyl), $L_2$-$(C_1$-$C_5$alkylene)-O—$(C_1$-$C_3$alkyl), $L_2$-$(C_1$-$C_5$alkylene)-O—$(C_3$-$C_6$cycloalkyl), $L_2$-$(C_1$-$C_5$alkylene)-SO$_2$—$(C_1$-$C_3$alkyl), $L_2$-$(C_1$-$C_5$alkylene)-OCF$_3$, or $L_2$-$(C_1$-$C_5$alkylene)-CN respectively, wherein $L_2$ is a suitable leaving group such as chloro, bromo, iodo or mesylate, in the presence of a suitable base;

Scheme 9'

(V')

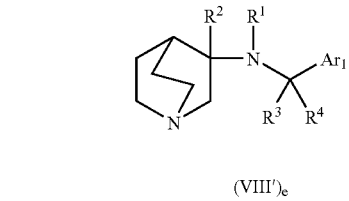

(VIII')$_e$ (vi) $R^1$ is a group of formula (i) —$C_1$-$C_6$alkylene)-OH can be prepared by oxidising intermediate (X) with a suitable oxidising agent;

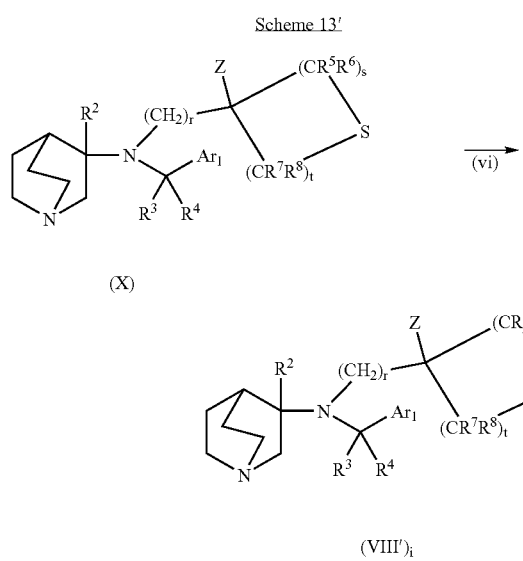

(vii) $Ar_1$ is a phenyl group substituted with a 1-pyrazole group can be prepared by reacting a compound of formula (VII')$_{m'}$, wherein $L_5$ is a suitable leaving group such as bromo, chloro or iodo, with pyrazole in the presence of a suitable base;

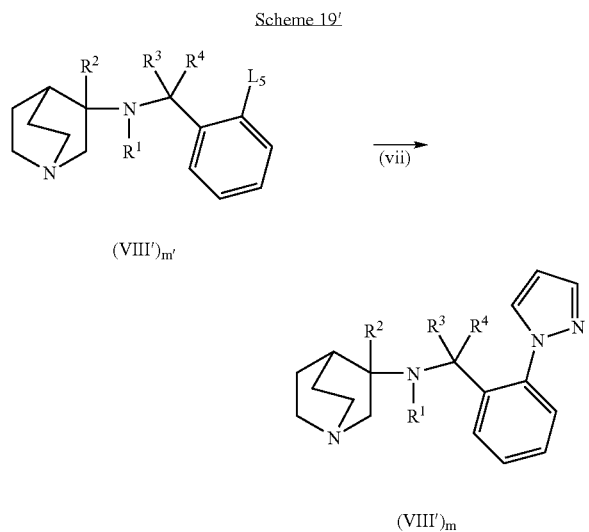

It will be appreciated that certain intermediates $Ar_1CR^3R^4L_6$, wherein $L_6$ is a suitable leaving group, such as for example mesylate, tosylate, bromo, chloro or iodo, used in the general methods mentioned above are not commercially available and need to be prepared according to suitable methods known in the art illustrated in the preparations and examples below. For example, the intermediate wherein $Ar_1$ is 2-phenyl-5-fluorophenyl, $R^3$ and $R^4$ are hydrogen, and $L_6$ is bromo can be prepared as illustrated in Scheme 21 below:

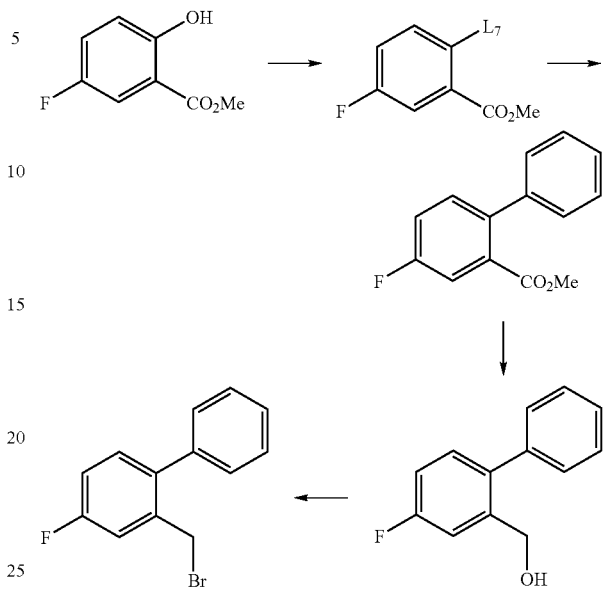

Methyl 5-fluorosalicylate was activated by converting the hydroxy group into a suitable leaving group $L_7$, such as for example a triflate, by reaction with a sulfonylating reagent such as N-phenyl trifluorosulfonimide in the presence of a base such as sodium hydride in a solvent such as DMF. The triflate was then reacted with phenyl boronic acid under palladium catalysis, using palladium acetate in the presence of tricyclohexyl phosphine and a base such as potassium fluoride in a solvent such as THF. The ester was then reduced to the benzyl alcohol with lithium aluminium hydride in a solvent such as THF. Finally the benzyl bromide was formed using a brominating agent such as triphenylphosphine dibromide in a solvent such as chloroform.

The following Preparations and Examples illustrate routes to the synthesis of the compounds of the invention.

Preparation 1: 1,1-Dimethylethyl (3S)-3-aminopiperidine-1-carboxylate a) 1,1-Dimethylethyl (3R)-3-hydroxypiperidine-1-carboxylate Solid ditert-butyldicarbonate (26.6 g, 122 mmol) was added in portions over 15 minutes to a stirred solution of (3R)-piperidin-3-ol hydrochloride (15.25 g, 111 mmol), triethylamine (30.9 mL, 222 mmol) and 4-(dimethylamino)-pyridine (50 mg) in dry dichloromethane (300 mL). After stirring for 18 hours at room temperature, the mixture was washed with aqueous citric acid, then brine. The organic extracts were dried (MgSO$_4$), filtered and evaporated in vacuo to give an oil. This was purified by flash chromatography on silica, eluting with ethyl acetate/cyclohexane (20:80 to 80:20), to give the title compound as a solid.

b) 1,1-Dimethylethyl (3R)-3-[(methylsulfonyl)oxy]-piperidine-1-carboxylate

Methanesulfonyl chloride (9.56 mL, 124 mmol) was added dropwise over 10 minutes to a stirred solution of 1,1-dimethylethyl (3R)-3-hydroxypiperidine-1-carboxylate (20.7 g, 103 mmol) and triethylamine (21.5 mL, 154 mmol) in dichloromethane (300 mL) at 0° C. After stirring for 3 hour at 0° C., the reaction was quenched by addition of water. The organic phase was washed with brine, dried (MgSO$_4$), filtered and evaporated in vacuo to give an oil. This was purified by flash chromatography on silica, eluting with ethyl acetate/cyclohexane (20:80 to 50:50), to give the title compound as an oil.

c) 1,1-Dimethylethyl (3S)-3-azidopiperidine-1-carboxylate

Sodium azide (7.65 g, 118 mmol) was added to a solution of 1,1-dimethylethyl (3R)-3-[(methylsulfonyl)oxy]-piperidine-1-carboxylate (21.9 g, 78.5 mmol) in dry dimethylformamide (120 mL) and the resultant suspension heated at 70° C. for 48 hours. After cooling to room temperature, the reaction mixture was diluted with water and extracted into ethyl acetate. The organic phase was washed two further times with water, then brine. The organic extracts were dried (MgSO$_4$), filtered and evaporated in vacuo to give an oil. This was purified by flash chromatography on silica, eluting with ethyl acetate/cyclohexane (10:90 to 50:50), to give the title compound as an oil.

d) 1,1-Dimethylethyl (3S)-3-aminopiperidine-1-carboxylate

A mixture of 1,1-dimethylethyl (3S)-3-azidopiperidine-1-carboxylate (7.5 g) and 10% palladium-on-carbon (0.75 g) in methanol (100 mL) was hydrogenated in a Parr apparatus at 70 p.s.i. for 16 hours. The catalyst was removed by filtration through Celite and the solvent evaporated in vacuo to give an oil. The resultant title compound was used in subsequent reactions without further purification.

Preparation 2:
2-(Bromomethyl)-4-fluoro-1,1'-biphenyl a) Methyl 5-fluoro-2-{[(trifluoromethyl)sulfonyl]oxy}benzoate 5-Fluorosalicylic acid methyl ester (28.2 g, 166 mmol) was dissolved in dry dimethylformamide (165 mL) and stirred as sodium hydride (60% in oil) (7.30 g, 1.1 eq) was added portionwise over 30 mins at 0° C. The reaction mixture was stirred for a further 30 mins at room temperature, then N-phenyl trifluoromethanesulfonimide (62.8 g, 1.05 eq) was added in portions over 30 mins, then left to stir for 3 hours. The mixture was diluted with diethyl ether and washed successively with water, then brine. The organic layers were combined, dried (MgSO$_4$), filtered and the solvent removed in vacuo. The resulting oil was purified by flash chromatography on silica, eluting with ethyl acetate/cyclohexane (10:90 to 40:60), to give the title compound as an oil.

b) Methyl 4-fluoro-[1,1'-biphenyl]-2-carboxylate

Palladium acetate (635 mg, 0.05 eq), tricyclohexyl-phosphine (952 mg, 0.06 eq), potassium fluoride (10.85 g, 3.3 eq) and phenyl boronic acid (7.6 g, 1.1 eq) were taken up in dry THF (150 mL) and the reaction mixture flushed with nitrogen for 5 mins. A solution of methyl 5-fluoro-2-{[(trifluoromethyl)sulfonyl]oxy}benzoate (170.12 g, 56.7 mmol) in THF (20 mL) was added in one portion and the reaction mixture stirred at reflux under nitrogen for 5 hours. The reaction mixture was cooled to room temperature, diluted with ethyl acetate, then washed with water, dried (MgSO$_4$), filtered and the solvent removed in vacuo. The resulting oil was purified by flash chromatography on silica, eluting with ethyl acetate/cyclohexane (3:97 to 10:90), to give the title compound as an oil.

c) (4-Fluoro-[1,1'-biphenyl]-2-yl)methanol

A solution of methyl 4-fluoro-[1,1'-biphenyl]-2-carboxylate (3 g, 13.1 mmol) in THF (20 mL) was added at 0° C. to a suspension of lithium aluminium hydride pellets (1 g, 26 mmol) in THF (30 mL). Upon addition the reaction mixture was heated at 60° C. under nitrogen for 2 h. The reaction was then cooled to 0° C. and the excess lithium aluminium hydride destroyed by adding water, then 1N sodium hydroxide (2 mL). The mixture was extracted into diethyl ether and the organic phase was dried (MgSO$_4$), filtered and the solvent removed in vacuo. The resulting oil was purified by flash chromatography on silica, eluting with ethyl acetate/heptane (2:98 to 25:75), to give the title compound as an oil.

d) 2-(Bromomethyl)-4-fluoro-1,1'-biphenyl

Triphenylphosphine dibromide (35.5 g, 2 eq) was added in one portion to a solution of (4-fluoro-[1,1'-biphenyl]-2-yl) methanol (8.5 g, 42 mmol) in chloroform (250 mL). The reaction mixture was heated at 60° C. and left to stir overnight. The solid was filtered off and the solvent removed in vacuo. The resulting oil was purified by flash chromatography on silica, eluting with ethyl acetate/cyclohexane (0:100 to 30:70), to give the title compound as an oil.

EXAMPLE 1

(3S)—N-(2-Methylpropyl)-N-{[2-(trifluoromethyl)-phenyl]methyl}piperidin-3-amine, fumarate a) 1,1-Dimethylethyl (3S)-3-({[2-(trifluoromethyl)-phenyl]methyl}amino)piperidine-1-carboxylate 1,1-Dimethylethyl (3S)-3-aminopiperidine-1-carboxylate (1.0 g, 5 mmol), 2-trifluoromethylbenzaldehyde (0.87 g, 5 mmol), 5% palladium on carbon (0.35 g) and ethanol (40 mL) were hydrogenated at 60 psi for 2.5 h. using a Parr hydrogenator. The catalyst was filtered off and the filtrate evaporated in vacuo. The resultant oil was purified by flash chromatography on silica, eluting with ethyl acetate/cyclohexane (0:100 to 75:25), to give the title compound as an oil.

b) 1,1-Dimethylethyl (3S)-3-((2-methylpropyl){[2-(trifluoromethyl)phenyl]methyl}amino)piperidine-1-carboxylate Sodium triacetoxyborohydride (0.23 g, 1.08 mmol) was added to a stirred solution of 1,1-dimethylethyl (3S)-3-({[2-(trifluoromethyl)phenyl]methyl}amino)piperidine-1-carboxylate (0.19 g, 0.53 mmol), isobutyraldehyde (0.12 g, 1.6 mmol) and 1,2-dichloroethane (5 mL). After stirring under nitrogen at room temperature for 1 day, the reaction mixture was diluted with methanol (6 mL) and absorbed onto a cationic ion exchange resin (Isolute™ SCX-2). After washing the cartridge with methanol (25 mL), the basic components were isolated by elution with 2N ammonia in methanol and the eluate evaporated to give an oil.

c) (3S)—N-(2-Methylpropyl)-N-{[2-(trifluoromethyl)-phenyl]methyl}piperidin-3-amine, fumarate 1,1-Dimethylethyl (3S)-3-((2-methylpropyl){[2-(trifluoromethyl)phenyl]methyl}amino)piperidine-1-carboxylate (0.139 mg, 0.335 mmol), trifluoroacetic acid (4 mL) and dichloromethane (10 mL) were stirred at room temperature for 1 day. The solution was evaporated in vacuo to give an oil, which was redissolved in methanol and filtered through a cationic ion exchange resin (Isolute™ SCX-2). The basic components were isolated by elution with 2N ammonia in methanol. The eluate was evaporated in vacuo and the resultant oil converted to the fumaric acid salt (crystallisation from ethanol/ether), to give the title compound as a white solid. $^1$H NMR (300 MHz, CD$_3$OD): $\delta_H$ 7.77-7.74 (d, H), 7.51-7.43 (m, 2H), 7.25-7.22 (t, 1H), 4.23 (s, 2H), 3.79-3.66 (q, 2H), 3.21-3.08 (m, 4H), 2.83-2.61 (m, 3H), 2.28-2.10 (m, 2H), 1.90-1.82 (m, 2H), 1.59-1.37 (m, 3H), 0.77-72 (t, 6H); MS: (M+H)=315.

The following Examples were similarly prepared as described above for Example 1, by reductive alkylation of 1,1-dimethylethyl (3S)-3-({[2-(trifluoromethyl)phenyl] methyl}amino)piperidine-1-carboxylate with the appropriate aldehyde or ketone, and subsequent deprotection:

EXAMPLE 2

(3S)—N-(3,3-Dimethylbutyl)-N-{[2-(trifluoromethyl)phenyl]methyl}piperidin-3-amine, D-tartrate $^1$HNMR (300 MHz, CD$_3$OD): δ$_H$ 7.79-7.86 (d, 1H), 7.47-7.56 (m, 2H), 7.27-7.32 (t, 2H), 4.30 (s, 2H), 3.73-3.84 (t, 2H), 3.16-3.28 (m, 2H), 2.71-2.89 (m, 3H), 2.47-2.52 (t, 2H), 1.84-1.97 (m, 2H), 1.47-1.63 (m, 2H), 1.22-1.33 (m, 2H), 0.75 (s, 9H); MS: [M+H]=343.

EXAMPLE 3

(3S)—N-Cyclohexyl-N-{[2-(trifluoromethyl)phenyl]-methyl}piperidin-3-amine, D-tartrate $^1$HNMR (300 MHz, CD$_3$OD): δ$_H$ 7.88-7.91 (d, 1H), 7.51-7.58 (m, 2H), 7.29-7.34 (t, 1H), 4.29 (s, 2H), 3.68-3.83 (q, 2H), 3.43-3.50 (m, 1H), 3.08-3.27 (m, 1H), 2.87-3.00 (m, 2H), 2.39-2.45 (dd, 1H), 2.22-2.29 (dd, 1H), 2.22-2.16 (m, 2H), 1.76-1.90 (m, 2H), 1.58-1.62 (m, 1H), 1.27-1.41 (m, 2H), 1.08-1.22 (m, 2H), 0.97-1.03 (1H), 0.63-0.74 (m, 4H); MS: [M+H]=341.

EXAMPLE 4

(3S)—N-{[5-Fluoro-2-(trifluoromethyl)phenyl]methyl}-N-tetrahydro-2H-pyran-4-ylpiperidin-3-amine, L-tartrate a) 1,1-Dimethylethyl (3S)-3-(tetrahydro-2H-pyran-4-ylamino)piperidine-1-carboxylate 1,1-Dimethylethyl-(3S)-3-aminopiperidine-1-carboxylate (2 g, 11 mmol), 4H-tetrahydropyran-4-one (1.1 g, 11 mmol) and dichloroethane (40 mL) were stirred under nitrogen at room temperature for 15 min. Sodium triacetoxyborohydride (2.9 g, 14 mmol) was added in 3 lots over 30 minutes and stirred overnight. The reaction was diluted with water (50 mL) and made basic by addition of 2N NaOH solution. After stirring for 1 h, the mixture was extracted into dichloromethane, and the combined organic extracts washed with brine, dried (MgSO$_4$), filtered and evaporated in vacuo to give the title compound as an oil.

b) (3S)—N-{[5-Fluoro-2-(trifluoromethyl)phenyl]methyl}-N-tetrahydro-2H-pyran-4-ylpiperidin-3-amine, L-tartrate 1,1-Dimethylethyl (3S)-3-(tetrahydro-2H-pyran-4-ylamino)piperidine-1-carboxylate was reductively alkylated with 5-fluoro-2-(trifluoromethyl)benzaldehyde, then deprotected and crystallised as its L-tartrate salt as described above for Example 1 b) and c), to give the title compound. $^1$HNMR (300 MHz, CD$_3$OD): δ$_H$ 7.74-7.75 (m, 2H), 7.05-6.98 (t, 1H), 4.50 (s, 2H), 3.99-3.85 (m, 4H), 3.43-2.58 (m, 8H), 2.02-1.42 (m, 8H); MS: [M+H]=361.

The following Examples were similarly prepared as described above for Example 4, by reductive alkylation of 1,1-dimethylethyl (3S)-3-(tetrahydro-2H-pyran-4-ylamino) piperidine-1-carboxylate with the appropriate benzaldehyde, and subsequent deprotection:

EXAMPLE 5

(3S)—N-[(2-Chloro-5-fluorophenyl)methyl]-N-tetrahydro-2H-pyran-4-ylpiperidin-3-amine, L-tartrate $^1$HNMR (300 MHz, CD$_3$OD): δ$_H$ 7.32-7.24 (m, 2H), 6.92-6.85 (t, 1H), 4.30 (s, 2H), 3.90-3.84 (m, 4H), 3.32-3.17 (m, 4H), 3.08-2.97 (m, 1H), 2.85-2.67 (m, 3H), 1.98-1.82 (m, 2H), 1.73-1.82 (m, 2H), 1.73-1.46 (m, 6H); MS: [M+H]=327/329.

EXAMPLE 6

(3S)—N-([1,1'-Biphenyl]-2-ylmethyl)-N-tetrahydro-2H-pyran-4-ylpiperidin-3-amine, sesqui-L-tartrate $^1$HNMR (300 MHz, CD$_3$OD): δ$_H$ 7.51-7.48 (d, 1H), 7.35-7.17 (m, 7H), 7.08-7.05 (d, 1H), 3.30 (s, 1.5H), 3.79-3.74 (dd, 2H), 3.69 (s, 2H), 3.25-3.10 (m, 9H), 3.20-3.09 (m, 2H), 2.91-2.77 (m, 2H), 2.66-2.51 (m, 3H); MS: [M+H]=351.

EXAMPLE 7

(3S)—N-[(2-Chlorophenyl)methyl]-N-tetrahydro-2H-pyran-4-ylpiperidin-3-amine, D-tartrate $^1$HNMR (300 MHz, CD$_3$OD): δ$_H$ 7.52-7.49 (d, 1H), 7.26-7.87 (m, 3H), 4.30 (s, 2H), 3.92-3.80 (m, 4H), 3.16-2.34 (m, 4H), 2.92-2.05 (m, 1H), 2.90-2.66 (m, 3H), 1.93-187 (m, 2H), 1.68-1.39 (m, 6H); MS: [M+H]=309/311.

EXAMPLE 8

(3S)—N-Tetrahydro-2H-pyran-4-yl-N-{[2-(trifluoromethyl)phenyl]methyl}piperidin-3-amine, D-tartrate $^1$HNMR (300 MHz, CD$_3$OD): δ$_H$ 7.98-7.95 (d, 1H), 7.71-7.62 (q, 2H), 7.47-7.42 (t, 1H), 4.44 (s, 2H), 4.14-3.98 (m, 4H), 3.43-3.29 (m, 4H), 3.11-2.82 (m, 4H), 2.06-2.03 (m, 2H), 1.82-1.66 (m, 6H); MS: [M+H]=343.

EXAMPLE 9

(3S)—N-Cyclopentyl-N-{[2-(trifluoromethyl)phenyl]-methyl}piperidin-3-amine, L-tartrate a) 1,1-Dimethylethyl (3S)-3-(cyclopentylamino)-piperidine-1-carboxylate 1,1-Dimethylethyl (3S)-3-aminopiperidine-1-carboxylate (2.1 g, 10.5 mmol), cyclopentanone (4.65 mL, 52.5 mmol), and 10% palladium on carbon (0.2 g) in methanol (80 mL) were hydrogenated at 60 psi overnight in a Parr hydrogenator. The catalyst was filtered off and the filtrate evaporated in vacuo. The resultant oil was purified by flash chromatography on silica, eluting with ethyl acetate/cyclohexane (15:85 to 30:70), to give the title compound as an oil.

b) 1,1-Dimethylethyl (3S)-3-(cyclopentyl{[2-(trifluoromethyl)phenyl]methyl}amino)piperidine-1-carboxylate 1,1-Dimethylethyl (3S)-3-(cyclopentylamino)-piperidine-1-carboxylate (155 mg, 0.577 mmol), 2-(trifluoromethyl) benzyl bromide (0.105 mL, 1.2 eq) and anhydrous potassium carbonate (128 mg, 1.6 eq) in acetonitrile (3 mL) were heated at refluxed under nitrogen for 2 days. The reaction mixture was cooled to room temperature, diluted with ethyl acetate and washed with water, then brine. The organic extracts were dried (MgSO$_4$), filtered and evaporated in vacuo. The resulting oil was purified by flash chromatography on silica eluting with ethyl acetate/cyclohexane (0:100 to 30:70), to give the title compound as an oil.

c) (3S)—N-Cyclopentyl-N-{[2-(tifluoromethyl)phenyl]-methyl}piperidin-3-amine, L-tartrate 1,1-Dimethylethyl (3S)-3-(cyclopentyl {[2-(trifluoromethyl)phenyl]methyl}amino)piperidine-1-carboxylate (160 mg, 0.38 mmol), trifluoroacetic acid (0.5 mL) and dichloromethane (2 mL) were stirred at room temperature overnight. The solution was evaporated in vacuo to give an oil, which was redissolved in methanol and filtered through a cationic ion exchange resin (Isolute™ SCX-2). The basic components were isolated by elution with 2N ammonia in methanol. The eluate was evaporated in vacuo and the resultant oil converted to the L-tartaric acid salt (freeze drying from acetonitrile/water 1:1), to give the title compound as a white solid. $^1$H NMR (300 MHz, CD$_3$OD): $\delta_H$ 7.89-7.86 (d, 1H), 7.54-7.46 (m, 2H), 7.30-7.25 (t, 1H), 4.34 (s, 2H), 3.90-3.78 (q, 2H), 3.30-3.18 (m, 4H), 3.05-2.87 (m, 1H), 2.81-2.59 (m, 2H), 1.95-1.79 (m, 2H), 1.68-1.30 (m, 9H); MS: [M+H]=327.

The following Examples were similarly prepared as described above for Example 9, by reaction of 1,1-dimethylethyl (3R)-3-(cyclopentylamino)piperidine-1-carboxylate with the appropriate benzyl bromide and subsequent deprotection:

EXAMPLE 10

(3S)—N-([1,1'-Biphenyl]-2-ylmethyl)-N-cyclopentyl-piperidin-3-amine, L-tartrate $^1$H NMR (300 MHz, CD$_3$OD): $\delta_H$ 7.57-7.55 (d, 1H), 7.35-7.13 (m, 7H), 7.06-7.03 (d, 1H), 4.30 (s, 2H), 3.58 (s, 2H), 3.12-2.98 (m, 3H), 2.82-2.73 (m, 1H), 2.65-2.42 (m, 2H), 1.79-1.75(m, 1H), 1.69-1.65 (m, 1H), 1.53-1.19(m, 10H); MS: [M+H]=335.

EXAMPLE 11

(3S)—N-Cyclopentyl-N-([5-fluoro-1,1'-biphenyl]-2-ylmethyl)-piperidin-3-amine, L-tartrate $^1$H NMR (300 MHz, CD$_3$OD): $\delta_H$ 7.35-7.24 (m, 4H), 7.18-7.15 (m, 2H), 7.09-7.04 (m, 1H), 6.92-6.85 (m, 1H), 4.28 (s, 2H), 3.55 (m, 2H), 3.22-3.06 (m, 3H), 2.82-2.77 (m, 1H), 2.68-2.58 (m, 2H), 1.88-1.68 (m, 2H), 1.57-1.19 (m, 10H); MS: [M+H]=353.

EXAMPLE 12

(3S)—N-(Tetrahydrofuran-3-ylmethyl)-N-{[2-(trifluoromethyl)phenyl]methyl}piperidin-3-amine, L-tartrate a) 1,1-Dimethylethyl (3S)-3-[(tetrahydrofuran-3-ylmethyl) amino]piperidine-1-carboxylate To 5% palladium on carbon (0.05 g) under nitrogen was added a solution of 1,1-dimethylethyl-(3S)-3-aminopiperidine-1-carboxylate (0.50 g, 2.5 mmol) and tetrahydrofuran-3-carboxaldehyde (50% w/w in water) (0.50 g, 2.5 mmol) in ethanol (20 mL). The reaction mixture was hydrogenated overnight at 60 psi in a Parr hydrogenator. The catalyst was removed by filtration through Celite and the solvent removed in vacuo to give 1,1-dimethylethyl (3S)-3-[(tetrahydrofuran-3-ylmethyl)amino]piperidine-1-carboxylate as a colourless, slightly cloudy oil.

b) (3S)—N-(Tetrahydrofuran-3-ylmethyl)-N-{[2-(trifluoromethyl)phenyl]methyl}piperidin-3-amine, L-tartrate To a solution of 1,1-dimethylethyl (3S)-3-[(tetrahydrofuran-3-ylmethyl)amino]piperidine-1-carboxylate (0.67 g, 2.36 mmol) in 1,2-dichloroethane (15 mL) was added 2-(trifluoromethyl)benzaldehyde (0.93 mL, 7.07 mmol). To this mixture was added a solution of sodium triacetoxyborohydride (1.50 g, 7.07 mmol) in dimethylformamide (3 mL) and left to stir under nitrogen, at room temperature, over the weekend. To the reaction mixture was added water (10 mL) and the solution stirred vigorously for several minutes. The chlorinated organic layer was absorbed directly onto a silica column and the product eluted with methanol/ethyl acetate (0:100 to 30:70). The resultant pale yellow oil was taken up in methanol and absorbed onto a cationic ion exchange resin (Isolute™ SCX-2). After washing the cartridge with methanol (25 mL), the basic components were isolated by elution with 2N ammonia in methanol and the eluate evaporated to give 1,1-dimethylethyl (3S)-3-{(tetrahydrofuran-3-ylmethyl) {[2-(trifluoromethyl)-phenyl]methyl}amino}piperidine-1-carboxylate as a colourless oil.

To a solution of this oil (0.82 g, 1.85 mmol) in dichloromethane (10 mL) was added trifluoroacetic acid (2.06 mL, 27.8 mmol). The reaction mixture was stirred overnight at room temperature, then the solvent removed in vacuo. The resulting oil was taken up in methanol and absorbed onto a cationic ion exchange resin (Isolute™ SCX-2). After washing the cartridge with methanol (50 mL), the basic components were isolated by elution with 2N ammonia in methanol. The eluate was evaporated in vacuo to give a colourless oil. The diastereomers were separated by hplc (Chiralpak AD-H column; 98% heptane, 2% ethanol and 0.2% diethylamine). The faster eluting isomer was taken up in methanol and to this was added a solution of L-tartaric acid (0.046 g, 0.31 mmol) in methanol. Solvent was removed in vacuo and the resulting oil triturated with diethyl ether. Filtration of the resultant suspension gave the title compound as a white solid.

$^1$HNMR (300 MHz, CD$_3$OD): $\delta_H$ 7.75 (1H, d), 7.58-7.50 (2H, m), 7.34-7.29 (1H, m), 4.30 (3H, s), 3.83 (2H, s), 3.70-3.53 (3H, m), 3.42-3.31 (2H, m), 3.16 (1H, m), 2.90-2.67 (3H, m), 2.54-2.34 (2H, m), 2.34-2.20 (1H, m), 1.95-1.84 (3H, m), 1.63-1.45 (3H, m); MS: [M+H]=343.

The following Examples were prepared from racemic 1,1-dimethylethyl 3-aminopiperidine-1-carboxylate, as described above in Example 1:

EXAMPLE 13

N-{[2-(Methyloxy)phenyl]methyl}-N-{[2-(trifluoromethyl)phenyl]methyl}piperidin-3-amine $^1$HNMR (300 MHz, CDCl$_3$) $\delta_H$ 8.04-7.95 (d, 1H), 7.57-7.54 (d, 1H), 7.48-7.44 (m, 2H), 7.28-7.11 (m, 2H), 6.93-6.88 (t, 1H), 6.83-6.80 (d, 1H), 3.94-3.86 (d, 2H), 3.20-3.18 (d, 1H), 2.94-2.90 (d, 1H), 2.68-2.55 (m, 2H), 2.49-2.40 (dt, 1H), 2.08-2.04 (d, 1H), 1.76-1.72 (d, 1H), 1.52-1.25 (m, 4H); MS: [M+H]=379.

EXAMPLE 14

N-Cyclohexyl-N-{[2-(trifluoromethyl)phenyl]methyl}-piperidin-3-amine $^1$HNMR (300 MHz, CDCl$_3$) $\delta_H$ 8.01-7.93 (d, 1H), 7.59-7.56 (d, 1H), 7.51-7.46 (t, 1H), 7.30-7.19 (m, 1H), 3.91 (s, 2H), 3.15-3.11 (d, 1H), 3.02-2.98 (d, 1H), 2.88-2.80 (d, 1H), 2.55-2.41 (m, 3H), 1.93-1.01 (m, 14); MS: [M+H]=341.

EXAMPLE 15

N-(Phenylmethyl)-N-{[2-(trifluoromethyl)phenyl]methyl}piperidin-3-amine $^1$HNMR (300 MHz, CDCl$_3$) $\delta_H$ 7.93-7.96 (d, 1H), 7.55-7.61 (d, 1H), 7.47-7.51 (t, 1H), 7.18-7.35 (m, 6H), 3.77-3.90

(q, 2H), 3.64-3.74 (q, 2H), 3.17-3.20 (d, 1H), 2.91-2.95 (d, 1H), 2.53-2.67 (m, 2H), 2.39-2.48 (dt, 1H), 1.97-2.06 (d, 1H), 1.22-1.82 (m, 3H); MS: [M+H]=349.

EXAMPLE 16

(3S)—N-(2-Methylpropyl)-N-{[2-(trifluoromethyl)phenyl]-methyl}-1-azabicyclo[2.2.2]octan-3-amine, sesquifumarate a) (3S)—N-{[2-(Trifluoromethyl)phenyl]methyl}-1-azabicyclo[2.2.2]octan-3-amine Sodium triacetoxyborohydride (18.7 g, 88.3 mmol) was added portionwise over 20 min. to a stirred solution of (3S)-1-azabicyclo[2.2.2]octan-3-amine dihydrochloride (5 g, 25.1 mmol) and 2-trifluoromethylbenzaldehyde (4.81 g, 27.6 mmol) in DMF (100 mL). After stirring under nitrogen for 4 days, the mixture was diluted with excess water, basified with 2N sodium hydroxide and stirred for 1 h. The product was extracted into dichloromethane and evaporated in vacuo to give an oil, which was dissolved in 2N hydrochloric acid. After washing with ether, the aqueous phase was basified with 2N sodium hydroxide and extracted with dichloromethane. The organic phase was dried (MgSO$_4$) and evaporated in vacuo to give an oil. $^1$HNMR (300 MHz, CD$_3$OD) $\delta_H$: 7.62-7.69 (t, 2H), 7.50-7.55 (t, 1H), 7.32-7.37 (t, 1H), 3.83-3.96 (q, 2H), 3.1-3.19 (m, 1H), 2.72-2.93 (m, 5H), 2.42-2.49 (m, 1H), 1.85-1.95 (m, 1H), 1.63-1.73 (m, 1H), 1.32-1.53); MS: [M+H]=285.

b) (3S)—N-(2-Methylpropyl)-N-{[2-(trifluoromethyl)-phenyl]methyl}-1-azabicyclo[2.2.2]octan-3-amine, sesquifumarate (3S)—N-{[2-(Trifluoromethyl)phenyl]methyl}1-azabicyclo[2.2.2]octan-3-amine (0.30 g, 1.06 mmol), isobutyraldehyde (0.152 g, 2.1 mmol) and 1,2-dichloroethane (6 mL) were stirred under nitrogen at room temperature for 15 min. Sodium triacetoxyborohydride (0.492 g, 2.32 mmol) was added in two lots over 5 min. TLC after 1 day showed the reaction to be incomplete, so additional sodium triacetoxyborohydride (0.24 g, 1.15 mmol) was added and the mixture heated at 50° C. for 5 days. After cooling to room temperature, methanol was added and the mixture was stirred for 1 h. This solution was filtered through a cationic ion exchange resin (Isolute™ SCX-2) and the basic fractions isolated by elution with 2N ammonia in methanol to give, after evaporation in vacuo, an oil. The crude product was purified using preparative LCMS to give the product as an acetate salt, which was converted to the free base using cationic ion exchange resin as described above. The free base was converted to the fumarate salt, to give the title compound as a white solid from ethanol/diethyl ether. $^1$HNMR (300 MHz, CD$_3$OD) $\delta_H$: 7.88-7.91 (d, 1H), 7.51-7.58 (m, H), 7.30-7.35 (t, 1H), 6.60 (s, 3H), 3.71-3.85 (q, 2H), 3.42-4.50 (m, 1H), 2.88-3.26 (m, 6H), 2.25-2.39 (m, 1H), 2.09-2.23 (m, 3H), 1.74-1.91 (m, 2H), 1.42-1.63 (m, 2H), 0.78-0.83 (t, 6H); MS: [M+H]=341.

The following Examples were similarly prepared as described above for Example 16, from (3S)—N-{[2-(trifluoromethyl)phenyl]methyl)}-1-azabicyclo-[2.2.2]octan-3-amine and the appropriate substituted benzaldehyde:

EXAMPLE 17

(3S)—N-([1,1'-Biphenyl]-2-ylmethyl)-N-(2-methylpropyl)-1-azabicyclo[2.2.2]octan-3-amine, D-tartrate $^1$HNMR (300 MHz, CD$_3$OD) $\delta_H$: 7.50-7.47 (d, 1H), 7.38-7.18 (m, 7H), 7.09-7.06 (dd, 1H), 4.29 (s, 2H), 3.58-3.54 (d, 1H), 3.43-3.39 (d, 1H), 3.25-3.18 (m, 1H), 3.09-3.90 (4H), 2.68-2.63 (t, 1H), 2.45-2.39 (dq, 1H), 2.16-1.98 (m, 3H), 1.83-1.74 (m, 2H), 1.65-1.61 (m, 1H), 1.45-1.42 (m, 1H), 1.31-1.22 (quin, 1H), 0.65-0.61 (t, 6H); MS: [M+H]=349.

EXAMPLE 18

(3S)—N-[(3,5-Dichlorophenyl)methyl]-N-(2-methylpropyl)-1-azabicyclo[2.2.2]octan-3-amine, sesqui D-tartrate $^1$HNMR (300 MHz, CD$_3$OD) $\delta_H$: 7.36-7.34 (m, 3H), 4.44 (s, 3H), 3.71 (s, 2H), 3.65-3.54 (m, 1H), 3.42-3.01 (m, 6H), 2.42-1.84 (m, 6H), 1.74-1.63 (m, 2H), 0.95-0.87 (dd, 6H); MS: [M+H]=341/343/345.

EXAMPLE 19

(3S)—N-[(2,4-Dichlorophenyl)methyl]-N-(2-methylpropyl)-1-azabicyclo[2.2.2]octan-3-amine $^1$HNMR (300 MHz, CDCl$_3$) $\delta_H$: 7.65-7.62 (d, 1H), 7.32-7.31 (d, 1H), 7.24-7.20 (dd, 1H), 3.72-3.56 (q, 2H), 3.08-3.01 (m, 1H), 2.87-2.55 (m, 6H), 2.35-2.20 (oct, 2H), 1.87-177 (m, 2H), 1.67-1.39 (3H), 1.25-1.17 (m, 1H), 0.87-0.82 (dd, 6H); MS: [M+H]=341/343/345.

EXAMPLE 20

(3S)—N-{[4-Fluoro-2-(trifluoromethyl)phenyl]methyl}-N-(2-methylpropyl)-1-azabicyclo[2.2.2]octan-3-amine, L-tartrate $^1$HNMR (300 MHz, CD$_3$OD) $\delta_H$: 7.94-7.89 (t, 1H), 7.34-7.27 (m, 2H), 4.29 (s, 4.29), 3.81-3.66 (q, 2H), 3.51-3.44 (t, 1H), 3.40-2.89 (m, 6H), 2.37-2.04 (m, 4H), 1.93-1.38 (m, 4H), 0.82-0.76 (dd, 6H); MS: [M+H]=359.

EXAMPLE 21

(3S)—N-[(4-Fluoro[1,1'-biphenyl]-2-yl)methyl]-N-(2-methylpropyl)-1-azabicyclo[2.2.2]octan-3-amine, L-tartrate $^1$HNMR (300 MHz, CD$_3$OD) $\delta_H$: 7.40-7.08 (m, 7H). 6.68-6.91 (dt, 1H), 4.29 (s, 2H), 3.56-4.0 (q, 2H), 3.31-2.96 (m, 5H), 2.72-2.67 (t, 1H), 2.58-2.52 (dq, 1H), 2.18-1.30 (m, 8H), 0.70-0.68 (dd, 6H); MS: [M+H]=367.

The compounds of the present invention are inhibitors of the uptake of one or more monoamines selected from serotonin, norepinephrine and dopamine. They work by selectively inhibiting one or more of the biogenic amine (serotonin, norepinephrine and dopamine) transporter proteins. Their selectivity profiles may be determined using the assays described below (see also J. Gobel, D. L. Saussy and A. Goetz, J. Pharmacol. Toxicolo. (1999), 42, 237-244). Compounds of Formula I and their pharmaceutically acceptable salts preferably exhibit a K$_i$ value less than 600 nM at one or more of these monoamine transporter proteins as determined using the scintillation proximity assay as described below.

The compounds of formula (I) exemplified above and their pharmaceutically acceptable salts exhibit a $K_i$ value less than 500 nM at one or more of these monoamine transporter proteins as determined using the scintillation proximity assay as described below. Especially preferred compounds of Formula I and their pharmaceutically acceptable salts exhibit a $K_i$ value less than 100 nM at one or more of these monoamine transporter proteins. Even more preferred compounds of Formula I and their pharmaceutically acceptable salts exhibit a $K_i$ value less than 50 nM at one or more of these monoamine transporter proteins. Preferably, compounds of the present invention which selectively inhibit one of the three biogenic amine transporters do so relative to the other two transporters by a factor of at least five, more preferably by a factor of at least ten. For example, a NET selective inhibitor has a ratio $K_i(SERT)/K_i(NET)$ and a ratio $K_i(DAT)/K_i(NET)$ greater than or equal to five, preferably greater than or equal to ten. Preferably, compounds of the present invention which selectively inhibit two of the three biogenic amine transporters do so relative to the other transporter by a factor of at least five, more preferably by a factor of at least ten. For example, a NET/SERT selective inhibitor has a ratio $K_i(DAT)/K_i(NET)$ and a ratio $K_i(DAT)/K_i(SERT)$ greater than or equal to five, preferably greater than or equal to ten Biogenic amine transporters control the amount of neurotransmitters in the synaptic cleft. Inhibition of the respective transporter leads to a rise in that neurotransmitter. Inhibition of the individual transporters can be studied by a simple competitive binding assay using selective radioligands for the individual expressed human transporter site. Compounds may be compared for selectivity and potency on the human norepinephrine transporter (hNET), the h-serotonin transporter (HSERT) and the h-dopamine transporter (hDAT) using membranes prepared from HEK293 cells expressing the respective transporter site.

Advantageously, the compounds of the present invention also have a reduced interaction (both as substrate and inhibitor) with the liver enzyme Cytochrome P450 (CYP2D6).

That is to say, they preferably exhibit less than 75% metabolism via the CYP2D6 pathway according to the CYP2D6 substrate assay described below and they preferably exhibit an IC50 of >6 µM according to the CYP2D6 inhibitor assay described below.

Generation of Stable Cell-lines Expressing the Human Dopamine, Norepinephrine and Serotonin Transporters Standard molecular cloning techniques were used to generate stable cell-lines expressing the human dopamine, norepinephrine and serotonin transporters. The polymerase chain reaction (PCR) was used in order to isolate and amplify each of the three full-length cDNAs from an appropriate cDNA library. Primers for PCR were designed using the following published sequence data:

Human dopamine transporter: GenBank M95167. Reference: Vandenbergh D J, Persico A M and Uhl G R. *A human dopamine transporter cDNA predicts reduced glycosylation, displays a novel repetitive element and provides racially-dimorphic TaqI RFLPs*. Molecular Brain Research (1992) volume 15, pages 161-166.

Human norepinephrine transporter: GenBank M65105. Reference: Pacholczyk T, Blakely, R D and Amara S G. *Expression cloning of a cocaine- and antidepressant-sensitive human noradrenaline transporter*. Nature (1991) volume 350, pages 350-354.

Human serotonin transporter: GenBank L05568. Reference: Ramamoorthy S, Bauman A L, Moore K R, Han H, Yang-Feng T, Chang A S, Ganaphthy V and Blakely R D. *Antidepressant- and cocaine-sensitive human serotonin transporter: Molecular cloning, expression, and chromosomal localization*. Proceedings of the National Academy of Sciences of the USA (1993) volume 90, pages 2542-2546.

The PCR products were cloned into a mammalian expression vector (eg pcDNA3.1 (Invitrogen)) using standard ligation techniques. The constructs were then used to stably transfect HEK293 cells using a commercially available lipofection reagent (Lipofectamine™-Invitrogen) following the manufacture's protocol.

Norepinephrine Binding Assay

The ability of compounds to compete with [$^3$H]-Nisoxetine for its binding sites on cloned human norepinephrine membranes has been used as a measure of its ability to block norepinephrine uptake via its specific transporter.

Membrane Preparation

Cell pastes from large scale production of HEK-293 cells expressing cloned human noradrenaline transporters were homogenised in 4 volumes 50 mM Tris.HCl containing 300 mM NaCl and 5 mM KCl, pH 7.4. The homogenate was centrifuged twice (40,000 g, 10 min, 4° C.) with pellet re-suspension in 4 volumes Tris.HCl buffer after the first spin and 8 volumes after the second spin. The suspended homogenate was centrifuged (100 g, 10 min, 4° C.) and the supernatant kept and re-centrifuged (40,000 g, 20 min, 4° C.). The pellet was resuspended in Tris.HCl buffer containing the above reagents along with 10% w/v sucrose and 0.1 mM phenylmethylsulfonyl fluoride (PMSF). The membrane preparation was stored in aliquots (1 ml) at −80° C. until required. The protein concentration of the membrane preparation was determined using a bicinchoninic acid (BCA) protein assay reagent kit (available from Pierce).

[$^3$H]-Nisoxetine Binding Assay

Each well of a 96 well microtitre plate was set up to contain the following:

| | |
|---|---|
| 50 µl | 2 nM [N-methyl-$^3$H]-Nisoxetine hydrochloride (70-87 Ci/mmol, from NEN Life Science Products) |
| 75 µl | Assay buffer (50 mM Tris.HCl pH 7.4 containing 300 mM NaCl and 5 mM KCl) |
| 25 µl | Test compound, assay buffer (total binding) or 10 µM Desipramine HCl (non-specific binding) |
| 50 µl | Wheatgerm agglutinin coated poly(vinyltoluene) (WGA PVT) SPA Beads (Amersham Biosciences RPNQ0001) (10 mg/ml) |
| 50 µl | Membrane (0.2 mg protein per ml.) |

The microtitre plates were incubated at room temperature for 10 hours prior to reading in a Trilux scintillation counter. The results were analysed using an automatic spline fitting programme (Multicalc, Packard, Milton Keynes, UK) to provide Ki values for each of the test compounds.

Serotonin Binding Assay

The ability of a test compound to compete with [$^3$H]-citalopram from its binding sites on cloned human serotonin membranes has been used as a measure of its ability to block serotonin uptake via its specific transporter (Ramamoorthy, S., Giovanetti, E., Qian, Y., Blakely, R., (1998) J. Biol. Chem. 273, 2458).

Membrane Preparation

The preparation of membrane is essentially similar to that for the norepinephrine transporter containing membrane described above. The membrane preparation was stored in aliquots (1 ml) at −70° C. until required. The protein concentration of the membrane preparation was determined using BCA protein assay reagent kit.

[$^3$H]-Citalopram Binding Assay

Each well of a 96 well microtitre plate was set up to contain the following:

| | |
|---|---|
| 50 μl | 2 nM [$^3$H]-Citalopram (60-86 Ci/mmol, Amersham Biosciences) |
| 75 μl | Assay buffer (50 mM Tris.HCl pH 7.4 containing 150 mM NaCl and 5 mM KCl) |
| 25 μl | Diluted compound, assay buffer (total binding) or 100 μM Fluoxetine (non-specific binding) |
| 50 μl | WGA PYT SPA Beads (40 mg/ml) |
| 50 μl | Membrane preparation (0.4 mg protein per ml) |

The microtitre plates were incubated at room temperature for 10 hours prior to reading in a Trilux scintillation counter. The results were analysed using an automatic spline fitting programme (Multicalc, Packard, Milton Keynes, UK) to provide Ki (nM) values for each of the test compounds.

Dopamine Binding Assay

The ability to compete with [$^3$H]-WIN35,428 for its binding sites on human cell membranes containing cloned human dopamine transporter has been used as a measure of its ability to block dopamine uptake via its specific transporter (Ramamoorthy et al 1998 supra).

Membrane Preparation.

Is essentially the same as for membranes containing cloned human serotonin transporter as described above.

[$^3$H]-WIN35,428 Binding Assay

Each well of a 96 well microtitre plate was set up to contain the following:

| | |
|---|---|
| 50 μl | 4 nM [$^3$H]-WIN35,428428 (84-87 Ci/mmol, from NEN Life Science Products) |
| 75 μl | Assay buffer (50 mM Tris.HCl pH 7.4 containing 150 mM NaCl and 5 mM KCl) |
| 25 μl | Diluted compound, assay buffer(total binding) or 100 μM Nomifensine (non-specific binding) |
| 50 μl | WGA PVT SPA Beads (10 mg/ml) |
| 50 μl | Membrane preparation (0.2 mg protein per ml.) |

The microtitre plates were incubated at room temperature for 120 minutes prior to reading in a Trilux scintillation counter. The results were analysed using an automatic spline fitting programme (Multicalc, Packard, Milton Keynes, UK) to provide Ki values for each of the test compounds.

CYP2D6 Assays

Cytochrome P450 2D6 (CYP2D6) is a mammalian enzyme which is commonly associated with the metabolism of around 30% pharmaceutical compounds. Moreover, this enzyme exhibits genetic polymorphism, resulting in the presence of both normal and poor metabolizers in the population. A low involvement of CYP2D6 in the metabolism of compounds (i.e. the compound being a poor substrate of CYP2D6) is desirable in order to reduce any variability from subject to subject in the pharmacokinetics of the compound. Also, compounds with a low inhibitor potential for CYP2D6 are desirable in order to avoid drug-drug interactions with co-administered drugs that are substrates of CYP2D6. Compounds may be tested both as substrates and as inhibitors of this enzyme by means of the following assays.

CYP2D6 Substrate Assay

Principle:

This assay determines the extent of the CYP2D6 enzyme involvement in the total oxidative metabolism of a compound in microsomes. Preferred compounds of the present invention exhibit less than 75% total metabolism via the CYP2D6 pathway.

For this in vitro assay, the extent of oxidative metabolism in human liver microsomes (HLM) is determined after a 30 minute incubation in the absence and presence of Quinidine, a specific chemical inhibitor of CYP2D6. The difference in the extent of metabolism in absence and presence of the inhibitor indicates the involvement of CYP2D6 in the metabolism of the compound.

Materials and Methods:

Human liver microsomes (mixture of 20 different donors, mixed gender) were acquired from Human Biologics (Scottsdale, Ariz., USA). Quinidine and β-NADPH (β-Nicotinamide Adenine Dinucleotide Phosphate, reduced form, tetrasodium salt) were purchased from Sigma (St Louis, Mo., USA). All the other reagents and solvents were of analytical grade. A stock solution of the test compound (TC) was prepared in a mixture of Acetonitrile/Water to reach a final concentration of acetonitrile in the incubation below 0.5%.

The microsomal incubation mixture (total volume 0.1 mL) contained the TC (4 μM), β-NADPH (1 mM), microsomal proteins (0.5 mg/mL), and Quinidine (0 or 2 μM) in 100 mM sodium phosphate buffer pH 7.4. The mixture was incubated for 30 minutes at 37° C. in a shaking waterbath. The reaction was terminated by the addition of acetonitrile (75 μL). The samples were vortexed and the denaturated proteins were removed by centrifugation. The amount of TC in the supernatant was analyzed by liquid chromatography/mass spectrometry (LC/MS) after addition of an internal standard. A sample was also taken at the start of the incubation (t=0), and analysed similarly.

Analysis of the TC was performed by liquid chromatography/mass spectrometry. Ten μL of diluted samples (20 fold dilution in the mobile phase) were injected onto a Spherisorb CN Column, 5 μM and 2.1 mm×100 mm (Waters corp. Milford, Mass., USA). The mobile phase consisting of a mixture of Solvent A/Solvent B, 30/70 (v/v) was pumped (Alliance 2795, Waters corp. Milford, Mass., USA) through the column at a flow rate of 0.2 ml/minute. Solvent A and Solvent B were a mixture of ammonium formate $5.10^{-3}$ M pH 4.5/methanol in the proportions 95/5 (v/v) and 10/90 (v/v), for solvent A and solvent B, respectively. The TC and the internal standard were quantified by monitoring their molecular ion using a mass spectrometer ZMD or ZQ (Waters-Micromass corp, Manchester, UK) operated in a positive electrospray ionisation.

The extent of CYP2D6 involvement (% of CYP2D6 involvement) was calculated comparing the extent of metabolism in absence and in presence of quinidine in the incubation.

The extent of metabolism without inhibitor (%) was calculated as follows:

$$\frac{(TC \text{ response in samples without inhibitor})_{time\ 0} - (TC \text{ response in samples without inhibitor})_{time\ 30}}{(TC \text{ response in samples without inhibitor})_{time\ 0}} \times 100$$

The extent of metabolism with inhibitor (%) was calculated as follows:

$$\frac{(TC \text{ response in samples without inhibitor})_{time\ 0} - (TC \text{ response in samples with inhibitor})_{time\ 30}}{(TC \text{ response in samples without inhibitor})_{time\ 0}} \times 100$$

where the TC response is the area of the TC divided by the area of the internal standard in the LC/MS analysis chromatogram, time0 and time30 correspond to the 0 and 30 minutes incubation time.

The % of CYP2D6 involvement was calculated as follows:

$$\frac{(\% \text{ extent of metabolism without inhibitor}) - (\% \text{ extent of metabolism with inhibitor})}{\% \text{ extent of metabolism without inhibitor}} \times 100$$

CYP2D6 Inhibitor Assay

Principle:

The CYP2D6 inhibitor assay evaluates the potential for a compound to inhibit CYP2D6. This is performed by the measurement of the inhibition of the bufuralol 1'-hydroxylase activity by the compound compared to a control. The 1'-hydroxylation of bufuralol is a metabolic reaction specific to CYP2D6. Preferred compounds of the present invention exhibit an IC$_{50}$ higher than 6 µM for CYP2D6 activity, the IC$_{50}$ being the concentration of the compound that gives 50% of inhibition of the CYP2D6 activity.

Material and Methods:

Human liver microsomes (mixture of 20 different donors, mixed gender) were acquired from Human Biologics (Scottsdale, Ariz.). β-NADPH was purchased from Sigma (St Louis, Mo.). Bufuralol was purchased from Ultrafine (Manchester, UK). All the other reagents and solvents were of analytical grade.

Microsomal incubation mixture (total volume 0.1 mL) contained bufuralol 10 µM, β-NADPH (2 mM), microsomal proteins (0.5 mg/mL), and the test compound (TC) (0, 5, and 25 µM) in 100 mM sodium phosphate buffer pH 7.4. The mixture was incubated in a shaking waterbath at 37° C. for 5 minutes. The reaction was terminated by the addition of methanol (75 µL). The samples were vortexed and the denaturated proteins were removed by centrifugation. The supernatant was analyzed by liquid chromatography connected to a fluorescence detector. The formation of the 1'-hydroxybufuralol was monitored in control samples (0 µM TC) and in the samples incubated in presence of the TC. The stock solution of TC was prepared in a mixture of Acetonitrile/Water to reach a final concentration of acetonitrile in the incubation below 1.0%.

The determination of 1' hydroxybufuralol in the samples was performed by liquid chromatography with fluorimetric detection as described below. Twenty five µL samples were injected onto a Chromolith Performance RP-18e column (100 mm×4.6 mm) (Merck KGAa, Darmstadt, Germany). The mobile phase, consisting of a mixture of solvent A and solvent B whose the proportions changed according the following linear gradient, was pumped through the column at a flow rate of 1 ml/min:

| Time (minutes) | Solvent A (%) | Solvent B (%) |
|---|---|---|
| 0 | 65 | 35 |
| 2.0 | 65 | 35 |
| 2.5 | 0 | 100 |
| 5.5 | 0 | 100 |
| 6.0 | 65 | 35 |

Solvent A and Solvent B consisted of a mixture of 0.02 M potassium dihydrogenophosphate buffer pH3/methanol in the proportion 90/10 (v/v) for solvent A and 10/90 (v/v) for solvent B. The run time was 7.5 minutes. Formation of 1'-hydroxybufuralol was monitored by fluorimetric detection with extinction at λ 252 nm and emission at λ 302 nm.

The IC$_{50}$ of the TC for CYP2D6 was calculated by the measurement of the percent of inhibition of the formation of the 1'-hydroxybufuralol in presence of the TC compared to control samples (no TC) at a known concentration of the TC.

The percent of inhibition of the formation of the 1'-hydroxybufuralol is calculated as follows:

$$\frac{(1'\text{-hydroxybufuralol formed without inhibitor}) - (1'\text{-hydroxybufuralol formed with inhibitor})}{(1'\text{-hydroxybufuralol area formed without inhibitor})} \times 100$$

The IC$_{50}$ is calculated from the percent inhibition of the formation of the 1'-hydroxybufuralol as follows (assuming competitive inhibition):

$$\frac{TC \text{ Concentration} \times (100 - \text{Percent of inhibition})}{\text{Percent of inhibition}}$$

The IC$_{50}$ estimation is assumed valid if inhibition is between 20% and 80% (Moody G C, Griffin S J, Mather A N, McGinnity D F, Riley R J. 1999. Fully automated analysis of activities catalyzed by the major human liver cytochrome P450 (CYP) enzymes: assessment of human CYP inhibition potential. Xenobiotica, 29(1): 53-75).

The invention claimed is:

1. A compound of formula (I):

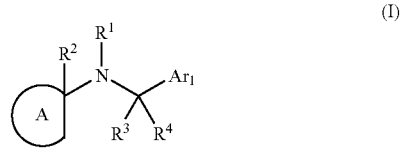

wherein

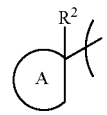

is a group of formula (a) or (b)

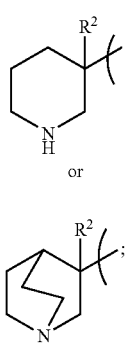

(a)

or

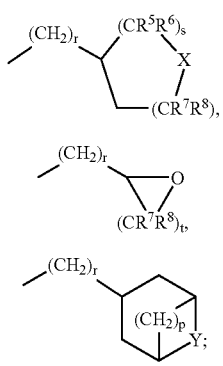

(b)

$R^1$ is $C_1$-$C_6$ alkyl, $C_2$-$C_6$ alkenyl, —$(CH_2)_m$—$CF_3$, —$(CH_2)_n$—S—$(C_1$-$C_3$ alkyl), —$CH_2$—COO—$(C_1$-$C_2$ alkyl), —$(C_1$-$C_5$ alkylene)-O—$(C_1$-$C_3$ alkyl), —$(C_1$-$C_5$ alkylene)-O—$(C_3$-$C_6$ cycloalkyl), —$(C_1$-$C_5$ alkylene)-$SO_2$—$(C_1$-$C_3$ alkyl), —$(C_1$-$C_5$ alkylene)-$OCF_3$, —$(C_1$-$C_6$ alkylene)-OH, —$(C_1$-$C_5$ alkylene)-CN, —$(CH_2)_q$—$Ar_2$ or a group of formula (ia), (ib) or (ii)

(ia)

(ib)

(ii)

$R^2$, $R^3$, and $R^4$ are each independently selected from hydrogen or $C_1$-$C_2$ alkyl;
$R^5$, $R^6$, $R^7$, and $R^8$ are at each occurrence independently selected from hydrogen or $C_1$-$C_2$ alkyl;
—X— is a bond, —$CH_2$—, —CH=CH—, —O—, —S—, or —$SO_2$—;
—Y— is a bond, —$CH_2$— or —O—;
p is 0, 1 or 2;
q is 0, 1 or 2;
r is 0 or 1;
s is 0, 1, 2 or 3;
m is 1, 2 or 3;
n is 1, 2 or 3;
t is 2, 3 or 4;
—$Ar_1$ is phenyl, pyridyl, thiazolyl or naphthyl; wherein said phenyl, pyridyl or thiazolyl group may be substituted with 1, 2 or 3 substituents each independently selected from halo, trifluoromethyl, cyano, $C_1$-$C_4$alkyl, —O—$(C_1$-$C_4$ alkyl), —O—$(C_1$-$C_4$ difluoroalkyl), —O—$(C_1$-$C_4$ trifluoroalkyl), —S—$(C_1$-$C_4$ alkyl), —S—$(C_1$-$C_2$ trifluoroalkyl) and/or with 1 substituent selected from pyridyl, pyrazole, phenyl (optionally substituted with 1, 2 or 3 halo substituents) and phenoxy (optionally substituted with 1, 2 or 3 halo substituents); and wherein said naphthyl group may be optionally substituted with 1, 2 or 3 substituents each independently selected from halo, trifluoromethyl, cyano, $C_1$-$C_4$ alkyl, —O—$(C_1$-$C_4$ alkyl), —O—$(C_1$-$C_4$ difluoroalkyl), —O—$(C_1$-$C_4$ trifluoroalkyl), —S—$(C_1$-$C_4$ alkyl), —S—$(C_1$-$C_2$ trifluoroalkyl);

$Ar_2$ is naphthyl, pyridyl, thiazolyl, furyl, thiophenyl, benzothiophenyl, or phenyl, wherein said naphthyl, pyridyl, thiazolyl, furyl, thiophenyl, benzothiophenyl, or phenyl may be substituted with 1, 2 or 3 substituents each independently selected from halo, $C_1$-$C_4$ alkyl, trifluoromethyl and —O—$(C_1$-$C_4$ alkyl).

2. The compound of claim 1, wherein $R^2$, $R^3$, $R^4$, $R^5$, $R^6$, $R^7$, and $R^8$ are each hydrogen.

3. The compound of claim 1, wherein $R^1$ is $C_1$-$C_6$ alkyl.

4. The compound of claim 1, wherein $R^1$ is a group of the formula (ib), r is 1, t is 3, and each $R^7$ and $R^8$ is hydrogen.

5. The compound of claim 1, wherein $R^1$ is —$(CH_2)_q$—$Ar_2$, and q is 1.

6. The compound of claim 5, wherein —$Ar_2$ is pyridyl, phenyl or phenyl substituted with 1, 2 or 3 substituents each independently selected from halo, trifluoromethyl, $C_1$-$C_4$alkyl or O—$(C_1$-$C_4$ alkyl).

7. The compound of claim 1, wherein —$Ar_1$ is phenyl; phenyl substituted with 1, 2 or 3 substituents each independently selected from halo, trifluoromethyl and $C_1$-$C_4$ alkyl and/or with 1 substituent selected from phenyl, phenyl substituted with 1, 2 or 3 halo substituents, pyridyl, pyrazole, phenoxy and phenoxy substituted with 1, 2 or 3 halo substituents; pyridyl; or pyridyl substituted with 1, 2 or 3 substituents each independently selected from halo, trifluoromethyl and $C_1$-$C_4$ alkyl and/or with 1 substituent selected from phenyl and phenyl substituted with 1, 2 or 3 halo substituents.

8. The compound of claim 1, wherein —$Ar_1$ is phenyl or phenyl substituted with 1, 2 or 3 substituents each independently selected from halo, trifluoromethyl and $C_1$-$C_4$ alkyl and/or with 1 substituent selected from phenyl, phenyl substituted with 1, 2 or 3 halo substituents, pyridyl, pyrazole, phenoxy and phenoxy substituted with 1, 2 or 3 halo substituents.

9. The compound of claim 1, wherein —$Ar_1$ is pyridyl or pyridyl substituted with 1, 2 or 3 substituents each independently selected from halo, trifluoromethyl and $C_1$-$C_4$ alkyl and/or with 1 substituent selected from phenyl and phenyl substituted with 1, 2 or 3 halo substituents.

10. A pharmaceutical composition, comprising a compound of claim 1 or a pharmaceutically acceptable salt thereof, together with a pharmaceutically acceptable diluent or carrier.

11. A compound of claim 1 wherein $R^1$ is a group of the formula (ia) and each $R^5$, $R^6$, $R^7$ and $R^8$ is hydrogen.

* * * * *